United States Patent [19]
Magerlein

[11] 3,933,889
[45] Jan. 20, 1976

[54] 4,5-CIS-DIDEHYDRO-PGF$_{1\alpha}$ ANALOGS

[75] Inventor: Barney J. Magerlein, Portage, Mich.

[73] Assignee: The Upjohn Company, Kalamazoo, Mich.

[22] Filed: Feb. 7, 1974

[21] Appl. No.: 440,629

Related U.S. Application Data

[63] Continuation-in-part of Ser. No. 247,993, April 27, 1972, abandoned.

[52] U.S. Cl. ...... 260/468 D; 260/211 R; 260/240 R; 260/247.2 R; 260/268 R; 260/293.65; 260/326.2; 260/373.2 R; 260/429.9; 260/439 R; 260/448 R; 260/448.8 R; 260/501.1; 260/501.15; 260/501.17; 260/501.2; 260/514 D; 424/305; 424/317

[51] Int. Cl.$^2$................ C07C 61/38; C07C 69/74

[58] Field of Search.................... 260/468 D, 514 D

[56] References Cited
UNITED STATES PATENTS
3,711,515    1/1973    Kelly................ 260/343.3

FOREIGN PATENTS OR APPLICATIONS
1,943,440    3/1970    Germany ............................ 260/468
2,136,136    1/1972    Germany ............................ 260/468
2,150,361    4/1972    Germany ............................ 260/468

OTHER PUBLICATIONS
March, Organic Chemistry, pp. 662–663, (1969).
Fieser et al., Reagents for Organic Synthesis, p. 671, (1967).

*Primary Examiner*—Robert Gerstl
*Attorney, Agent, or Firm*—Morris L. Nielsen

[57] ABSTRACT

This invention is a group of 4,5-didehydro PG$_1$ (prostaglandin-type) analogs having variable chain length, branching and fluoro substitution in the hydroxy-substituted side-chain, and processes for making them. These compounds are useful for a variety of pharmacological purposes, including anti-ulcer, inhibition of platelet aggregation, increase of nasal patency, labor inducement at term, and wound healing.

10 Claims, No Drawings

4,5-CIS-DIDEHYDRO-PGF$_{1\alpha}$ ANALOGS

CROSS REFERENCE TO RELATED APPLICATIONS

This application is a continuation-in-part of co-pending application Ser. No. 247,993, filed Apr. 27, 1972 now abandoned.

BACKGROUND OF THE INVENTION

This invention relates to novel compositions of matter, to novel methods for producing those, and to novel chemical intermediates useful in those processes. Particularly, this invention relates to certain novel analogs of some of the known prostaglandins in which a cis carbon-carbon double bond links C-4 and C-5 in the carboxy-terminated chain.

The known prostaglandins include, for example, prostaglandin E$_2$ (PGE$_2$), prostaglandin F$_2$ alpha and beta (PGF$_{2\alpha}$ and PGF$_{2\beta}$), prostaglandin A$_2$ (PGA$_2$), prostaglandin B$_2$ (PGB$_2$), and the corresponding PGE compounds. Each of the abovementioned known prostaglandins is a derivative of prostanoic acid which has the following structure and atom numbering:

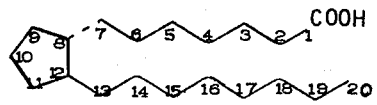

I

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE$_2$ has the following structure:

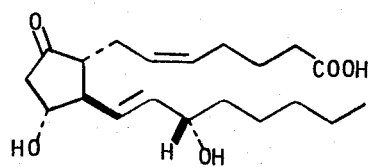

II

PGF$_{2\alpha}$ has the following structure:

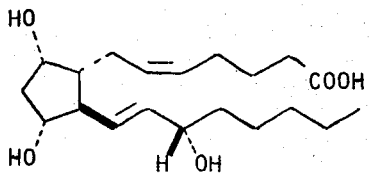

III

PGF$_{2\beta}$ has the following structure:

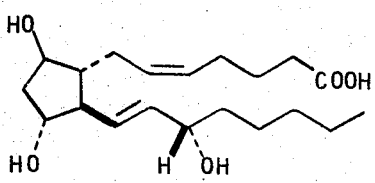

IV

PGA$_2$ has the following structure:

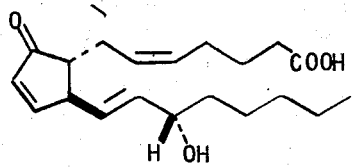

V

PGB$_2$ has the following structure:

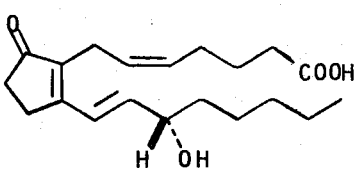

VI

Each of the known PG$_1$ prostaglandins, PGE$_1$, PGF$_{1\alpha}$, PGF$_{1\beta}$, PGA$_1$, and PGB$_1$, has a structure the same as that shown for the corresponding PG$_2$ compound except that, in each, the cis carbon-carbon double bond between C-5 and C-6 is replaced by a single bond. For example, PGE$_1$ has the following structure:

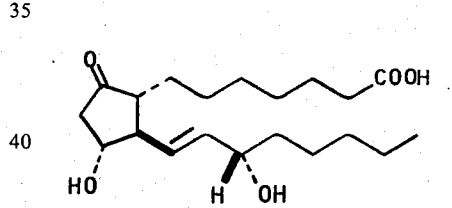

VII

In formulas II to VII, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in formulas II to VII is in S configuration. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e., the dextrorotatory and levorotatory forms. As drawn, formulas II to VII each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VII represents the other enantiomer of that prostaglandin.

The racemic form of a prostaglandin contains equal numbers of both enantiomeric molecules, and one of formulas II to VII and the mirror image of that formula is needed to represent correctly the corresponding racemic prostaglandin. For convenience hereinafter, use of the terms $PGE_1$, $PGE_2$, $PGE_3$, $PGF_2\beta$, and $PGF_3\alpha$, will mean the optically active form of that prostaglandin with the same absolute configuration as $PGE_1$ obtained from mammalian tissues. When reference to the racemic form of one of those prostaglandins is intended, the word "racemic" or "dl" will preceed the prostaglandin name, thus, racemic $PGE_1$ or dl-$PGF_{2\alpha}$.

$PGE_1$, $PGE_2$, and the corresponding $PGF\alpha$, $PGF\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., cited above. A few of those biological responses are systemic arterial blood pressure lowering in the case of the PGE, $PGF\beta$, and PGA compounds as measured, for example, in anesthetized (pentobarbital sodium) pentolinium-treated rats with indwelling aortic and right heart cannulas; pressor activity, similarly measured, for the $PGF_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE, $PGF\alpha$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma; bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc); xanthine derivatives (theophylline and aminophyllin); and corticosteroids (ACTH and predinisolone). Regarding use of these compounds see South African Pat. No. 68/1055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF\alpha$, and $PGF\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, $PGF\alpha$, and $PGF\beta$ compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to the new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE, PGA, and $PGF_\beta$ compounds are useful as hypotensive agents to reduce blood pressure in mammals, including man. For this purpose, the compounds are administered by intravenous infusion at the rate about 0.01 to about 50 µg. per kg. of body weight per minute, or in single or multiple doses of about 25 to 500 µg. per kg. of body weight total per day.

The PGA compounds and derivatives and salts thereof increase the flow of blood in the mammalian kidney, thereby increasing volume and electrolyte content of the urine. For that reason, PGA compounds are useful in managing cases or renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephric states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, $PGF_\alpha$, and $PGF_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 µg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

4,5-Didehydro-PGE$_1$ is mentioned in the prior art (see van Dorp, Annals N.Y. Acad. Sci. vol. 180, page 181, esp. pp. 184–185, 1971).

SUMMARY OF THE INVENTION

It is a purpose of this invention to provide novel 4,5-didehydro PG$_1$ analogs in which cis carbon-carbon double bond links C-4 and C-5 in the carboxy-terminated chain and in which there is variable chain length, branching, and fluoro substitution in the hydroxy-substituted side chain. It is a further purpose to provide 4,5-didehydro-13,14-dihydro-PG$_1$ analogs. It is a further purpose to provide esters, lower alkanoates, and pharmacologically acceptable salts of said analogs. It is a further purpose to provide novel processes for preparing these acids and esters. It is still a further purpose to provide novel intermediates useful in said processes.

The presently described acids and esters of the 4,5-unsaturated prostaglandin analogs include compounds of the following formulas, and also the racemic compounds of each respective formula and the mirror image thereof:

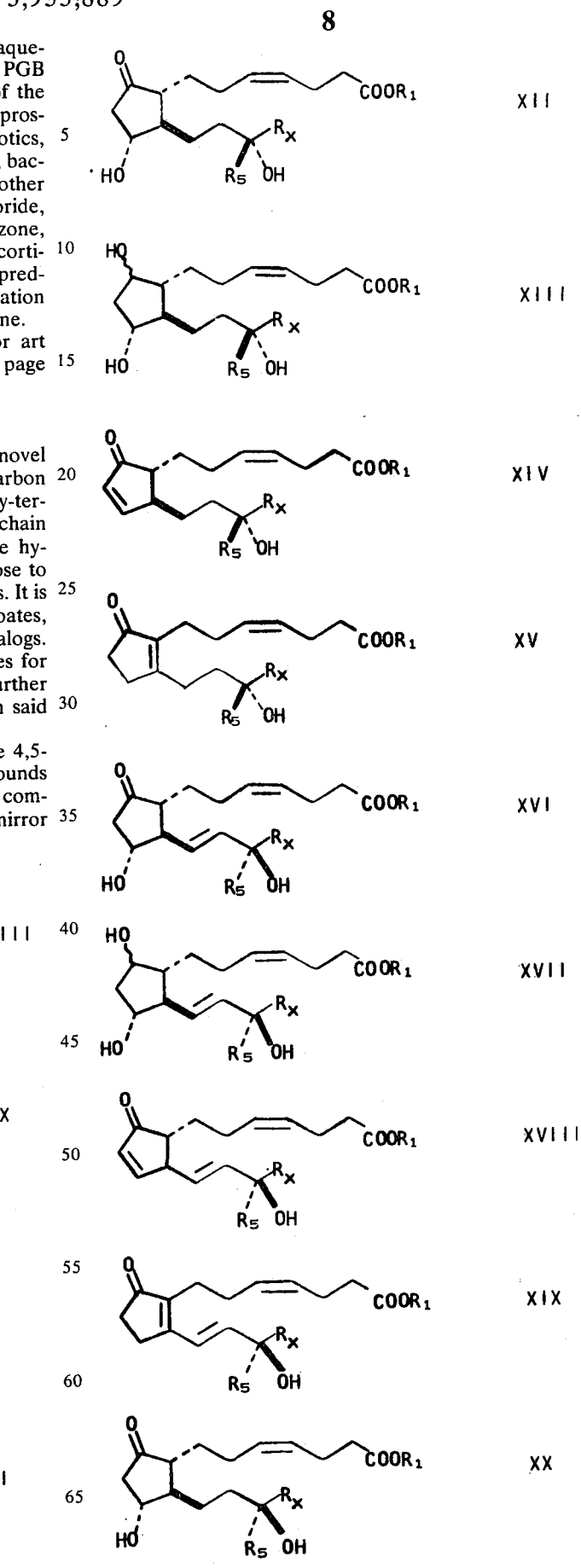

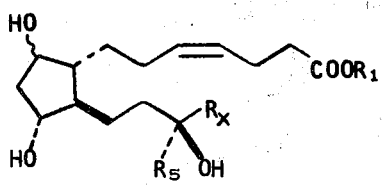

XXI

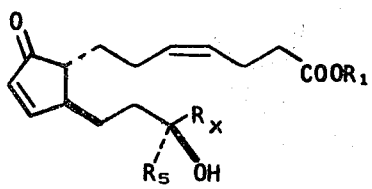

XXII

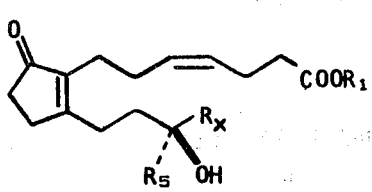

XXIII

In Formulas VIII to XXIII, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive; $R_5$ is hydrogen, methyl, or ethyl; $R_x$ is (1) alkyl of 2 to 4 carbon atoms, inclusive, substituted with zero to 2 fluoro, inclusive, (2) branched-chain alkyl of 5 carbon atoms or alkyl of 5 carbon atoms substituted with one or 2 fluoro, or (3) alkyl of 6 to 10 carbon atoms, inclusive, substituted with zero to 2 fluoro, inclusive; and the wavy line ~ indicates attachment to the cyclopentane ring in alpha or beta configuration.

Formula IX represents 4,5-cis-didehydro-18,19,20-trinor-PGF$_{1\alpha}$ when $R_1$ and $R_5$ are hydrogen, $R_x$ is -CH$_2$CH$_3$, and ~ indicates the alpha configuration. Formula XII represents 4,5-cis-didehydro-13,14-dihydro-16-fluoro-PGE$_1$ when $R_1$ and $R_5$ are hydrogen, and $R_x$ is -CHF-(CH$_2$)$_3$-CH$_3$. Formula XVII represents 4,5-cis-didehydro-20-methyl-15$\beta$-PGF$_{1\beta}$, methyl ester, when $R_1$ is methyl, $R_5$ is hydrogen, $R_x$ is -(CH$_2$)$_5$-CH$_3$ and ~ indicates the beta configuration.

In the name of the formula-IX example above, "trinor" indicates absence of three carbon atoms from the hydroxy-substituted side chain of the PGF$_1$ structure. Following the atom numbering of the prostanoic acid structure, then, C-18, C-19, and C-20 are construed as missing, and the methylene at C-17 is replaced with a terminal methyl group. In this system of nomenclature, the words "nor", "dinor", "trinor", "tetranor", and "pentanor" in the names for prostaglandin analogs are to be construed as indicating the number of carbon atoms missing from the C-16 to C-20 position of the prostanoic acid carbon skeleton.

Following the conventional numbering of the carbon atoms in the prostanoic acid structure, C-16 designates the carbon atom adjacent to the hydroxy-substituted carbon atom (C-15); C-17 designates the carbon atom once-removed from C-15.

As in the case of formulas II to VII, formulas VIII to XV are each intended to represent optically active prostanoic acid derivatives with the same absolute configuration as PGE$_1$ obtained from mammalian tissues. Furthermore, formulas VIII to XV represent compounds wherein the hydroxyl is attached to the side chain in alpha configuration. Also included within this invention are the 15-epimer compounds corresponding to

of formulas XVI to XXIII wherein the C-15 hydroxyl is in beta configuration. Hereinafter "15$\beta$" refers to the epimeric configuration. Thus, "4,5-cis-didehydro-15$\beta$-20-methyl-PGF$_{1\alpha}$" identifies a compound of formula XVII, similar to that of formula IX when $R_1$, $R_5$, and $R_x$ are the same as in formula IX except that it has the beta configuration at C-15 instead of the natural alpha configuration of 4,5-cis-didehydro-20-methyl-PGF$_{1\alpha}$. Each of formulas VIII to XV plus its mirror image describe a racemic compound within the scope of this invention; likewise each of the 15-epimer formulas corresponding to formulas XVI to XXIII plus its mirror image describe a racemic compound within the scope of this invention. For convenience hereinafter, such a racemic compound is designated by the prefix "racemic" (or "dl") before its name; when that prefix is absent, the intent is to designate an optically active compound represented by the appropriate formula VIII to XXIII.

With regard to formulas VIII to XXIII, examples of alkyl to one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of $R_x$ are ethyl, propyl, butyl, hexyl, heptyl, octyl, nonyl, decyl, and isomeric forms thereof; 1-ethylpropyl, 2,2-dimethylpropyl, and 1-methylbutyl; examples of alkyl substituted with zero to 2 fluoro, inclusive, are 1-fluoroethyl, 2-fluoroethyl, 1,1-difluoroethyl, 2,2-difluoroethyl, 1,2-difluorethyl, 1-fluoro-1-methylethyl, 2-fluoro-1-methylethyl, 1-fluoropropyl, 2,2-difluoropropyl, 3-fluoropropyl, 1-fluorobutyl, 2-fluorobutyl, 3-fluorobutyl, 4-fluorobutyl, 3,3-difluorobutyl, 3,4-difluorobutyl, 1-fluoro-1-methylbutyl, 1-fluoromethylbutyl, 2-fluoro-1-methylbutyl, 3-fluoro-1-methylbutyl, 4-fluoro-1-methylbutyl, 1-fluoropentyl, 2-fluoro-1-methylpentyl, 1-fluoro-2-ethylpentyl, 2,2-difluoro-1-propylpentyl, 3-fluorohexyl, 2-fluoroheptyl, 1,1-difluorooctyl, 2,2-difluorononyl, and 1,2-difluorodecyl.

Accordingly, there is provided an optically active compound of the formula

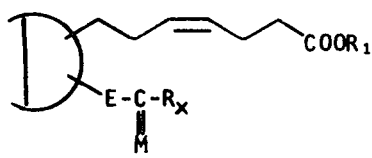
XXIV or a racemic compound of that formula and the mirror image thereof, wherein D is one of the four carbocyclic moieties:

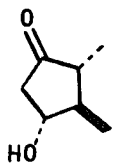 , 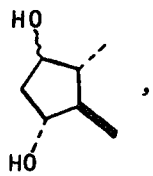 , 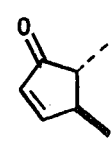 , or 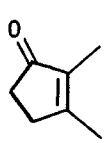 , wherein ~ indicates attachment of hydroxyl to the ring in alpha or beta configuration; wherein M is

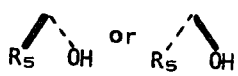

wherein $R_5$ is hydrogen, methyl, or ethyl; wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_x$ is (1) alkyl of 2 to 4 carbon atoms, inclusive, substituted with zero to 2 fluoro, inclusive, (2) branched-chain alkyl of 5 carbon atoms or alkyl of 5 carbon atoms substituted with one or 2 fluoro, or (3) alkyl of 6 to 10 carbon atoms, inclusive, substituted with zero to 2 fluoro, inclusive; and wherein E is trans-CH=CH- or -CH$_2$CH$_2$-; including the lower alkanoates thereof, and the pharmacologically acceptable salts thereof when $R_1$ is hydrogen.

Formula XXIV, which is written in generic form for convenience, represents PGE-type compounds when D is

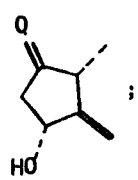

PGF-type compounds when D is

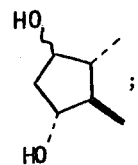

PGA-type compounds when D is

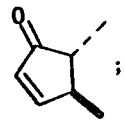

and PGB-type compounds when D is

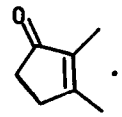

There is also provided an optically active compound of the formula

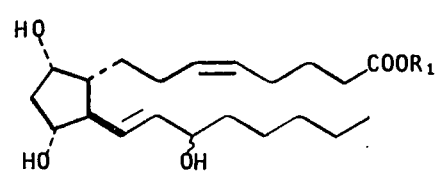
XXV or a racemic compound of that formula and the mirror image thereof, wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein ~ indicates attachment of hydroxyl in alpha or beta configuration.

The name of the formula-XXV compound above when $R_1$ is hydrogen and ~ is alpha is "4,5-cis-didehydro-2a-homo-PGF$_{1\alpha}$". In that name, "2a-homo" indicates an additional carbon atom in the carboxy-terminated side chain specifically between the C-2 and C-3 carbon atoms. There are, therefore, eight carbon atoms in the carboxy side chain instead of the normal seven in the prostanoic acid structure. From the end of the chain to the double bond they are identified as C-1, C-2, C-2a, C-3, and C-4. The carbon atoms connected by the cis double bond are C-4 and C-5, and the carbon atoms between the double bond and the ring are C-5, C-6, and C-7.

There is further provided an optically active compound of the formula

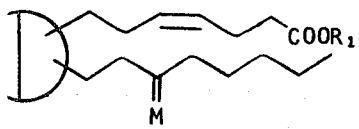

or a racemic compound of that formula and the mirror image thereof, wherein ⟩ is one of the four carbocyclic moieties:

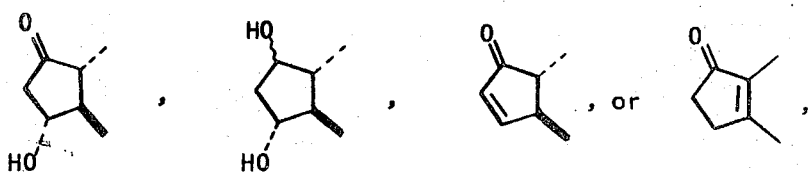, or 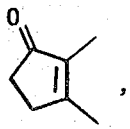, wherein ~ indicates attachment of hydroxyl to the ring in alpha or beta configuration; wherein M is

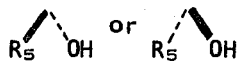

wherein $R_5$ is hydrogen, methyl, or ethyl; and wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof when $R_1$ is hydrogen.

The novel formula VIII-to-XXVI compounds and the racemic compounds of this invention each cause the biological responses described above for the PGE, $PGF\alpha$, $PGF\beta$, PGA, and PGB compounds, respectively, and each of these novel compounds is accordingly useful for the above-described corresponding purposes, and is used for those purposes in the same manner as described above.

The known PGE, $PGF\alpha$, $PGF\beta$, PGA, and PGB compounds are all potent in causing multiple biological responses even at low doses. For example, $PGE_1$ and $PGE_2$ both cause vasodepression and smooth muscle stimulation at the same time they exert antilipolytic activity. Moreover, for many applications, these known prostaglandins have an inconveniently short duration of biological activity. In striking contrast, the novel prostaglandin analogs of formulas VIII to XXVI and their racemic compounds, are substantially more specific with regard to potency in causing prostaglandin-like biological responses, and have a substantially longer duration of biolgical activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

To obtain the optimum combination of biological response specificity, potency, and duration of activity, certain compounds within the scope of formulas VIII to XXIII are preferred. For example, it is preferred that the hydroxyl at C-15 be in the alpha configuration.

Another preference is that any branching of the hydroxy-substituted chain be at either C-16 or C-17, or at both C-16 and C-17. In the general expression $R_x$ as used herein, in Charts A-F, examples of such branching are —CH(CH$_3$)—CH$_3$, —CH(CH$_3$)—C$_2$H$_5$, —CH$_2$—CH(CH$_3$)—CH$_3$, —C(CH$_3$)$_2$—CH$_2$—CH$_3$,

—CH(CH$_3$)—CH(CH$_3$)—CH$_3$, —C(CH$_3$)$_2$—C(CH$_3$)$_2$—CH$_2$-CH$_3$, —CH(CH$_3$)—(CH$_2$—CH$_3$, and —C(CH$_3$)$_2$—(CH$_2$)$_6$—CH$_3$. Especially preferred are those wherein the $R_x$ chain length is 4 to 6 carbon atoms.

Another preference is that any fluorine substitution on carbon atoms of the hydroxy-substituted chain be at either C-16 or C-7, or at both C-16 and C-17. Examples of $R_x$ having such fluorine substitution are -CHF-CH$_3$, —CH$_2$—CH$_2$F, —CF$_2$—CH$_3$, —CH$_2$—CHF$_2$, —CHF—CH$_2$F, —CHF—C$_2$H$_5$, —CH$_2$—CHF—CH$_3$, —CF$_2$—CH$_2$—CH$_3$, —CHF-CHF-CH$_3$, —CHF-(CH$_2$)$_3$—CH$_3$, —CF$_2$—(CH$_2$)$_3$—CH$_3$, —CH$_2$—CHF-(CH$_2$)$_2$—CH$_3$, —CH$_2$—CF$_2$—(CH$_2$)$_2$—CH$_3$, —CHF—CHF—(CH$_2$)$_2$—CH$_3$ and —CHF—(CH$_2$)$_8$—CH$_3$.

Especially preferred are those wherein the $R_x$ chain length is 4 to 6 carbon atoms.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 4,5-didehydro and 4,5-didehydro-13,14-dihyro $PGE_1$, $PGF_{1\alpha}$, $PGF_{1\beta}$, $PGA_1$, and $PGB_1$-type analogs encompassed by Formulas VIII to XXVI including their alkanoates, are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these Formula VIII-to-XXVI compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono- di-, and triethanolamine, ethyldiethanolamine, N-butylethanolamine, 2-amino-1-butanol, 2-amino-2-ethyl-1,3-propanediol, 2-amino-2-methyl-propanol, 1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds encompassed by Formulas VIII to XXVI are used for the purposes described above in free hydroxy form or also in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of Formulas VIII to XXVI are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the Formula VIII-to-XXVI compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used.

The 4,5-didehydro and 4,5-didehydro-13,14-dihydro PGE$_1$-, PGF$_{1\alpha}$ -, PGF$_{1\beta}$ -, PGA$_1$-, and PGB$_1$-type analogs encompassed by formulas VIII to XXVI are produced by the reactions and procedures described and exemplified hereinafter.

Reference to Chart A, herein, will make clear the steps for preparing the formula-XXVII through XXXV intermediates.

Previously, the preparation of an intermediate bicyclic lactone diol of the formula

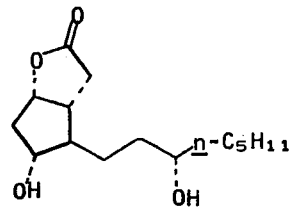

was reported by E. J. Corey et al., J. Am. Chem. Soc. 91, 5675 (1969), and later disclosed in an optically active

CHART A

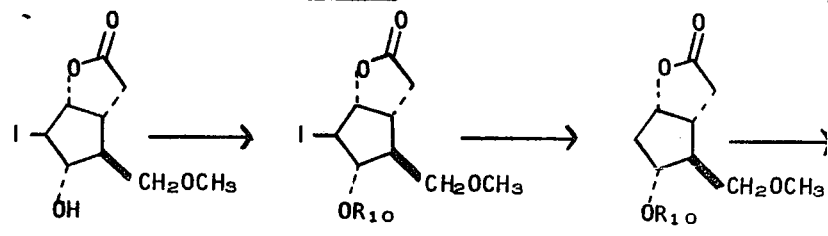

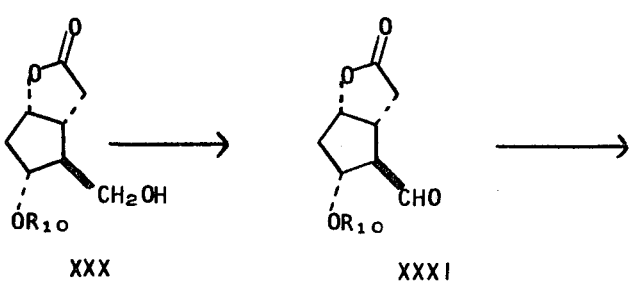

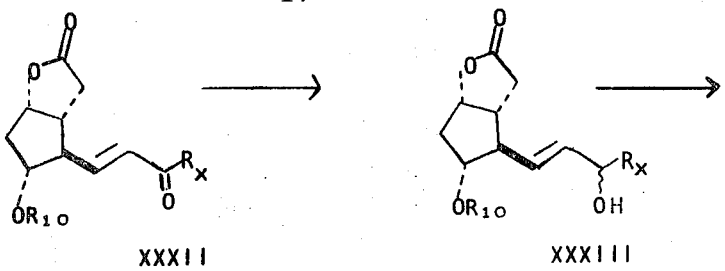

XXXII → XXXIII

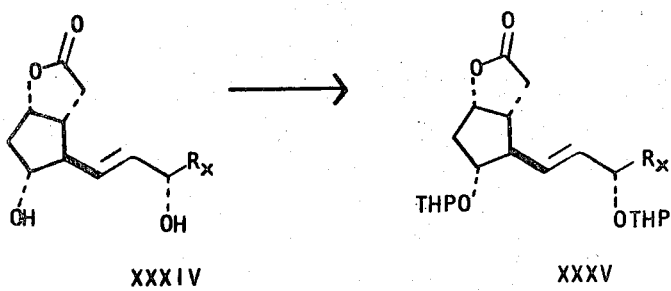

XXXIV → XXXV form by E. J. Corey et al., J. Am. Chem. Soc. 92, 397 (1970). Conversion of this intermediate to PGE₂ and PGF₂α, either in racemic or optically active form, was disclosed in those publications.

The iodolactone of formula XXVII in Chart A is known in the art (see Corey et al., above). It is available in either racemic or optically active (+ or −) form. For racemic products, the racemic form is used. For prostaglandins of natural configuration, the laevorotatory form (-) is used.

The formula-XXVIII compound (Chart A) bears an $R_{10}O$-moiety at the 4-position, wherein $R_{10}$ is

wherein T is alkyl of one to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms;

wherein $R_{12}$ is alkyl of one to 4 carbon atoms, inclusive;

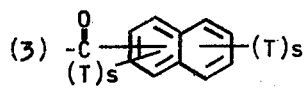

wherein T and s are as defined above; or (4) acetyl. In preparing the formula-XXVIII compound by replacing the hydrogen of the hydroxyl group in the 4-position with the acyl group $R_{10}$, methods known in the art are used. Thus, an aromatic acid of the formula $R_{10}OH$, wherein $R_{10}$ is as defined above, for example benzoic acid, is reacted with the formula-XXVII compound in the presence of a dehydrating agent, e.g. sulfuric acid, zinc chloride, or phosphoryl chloride; or an anhydride of the aromatic acid of the formula $(R_{10})_2O$, for example benzoic anhydride, is used.

Preferably, however, an acyl halide, e.g. $R_{10}Cl$, for example benzoyl chloride, is reacted with the formula-XXVII compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess.

As examples of $R_{10}$, the following are available as acids ($R_{10}OH$), anhydrides ($(R_{10})_2O$), or acyl chlorides ($R_{10}Cl$): benzoyl; substituted benzoyl, e.g. (2-, 3- or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)tolyl, (2-, 3-, or 4-)phenethylbenzoyl, 2-, 3-, or 4-nitrobenzoyl, (2,4- 2,5- or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

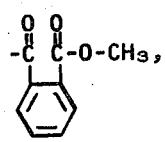

isophthaloyl, e.g.

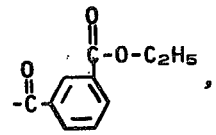

or terephthaloyl, e.g.

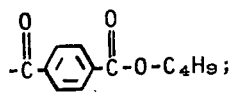

(1- or 2-)naphthoyl; substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isoproypl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl, and acetyl. There may be employed, therefore, benzoyl chloride, 4-nitrobenzoyl chloride, 3,5-dinitrobenzoyl chloride, and the like, i.e. $R_{10}Cl$ compounds corresponding to the above $R_{10}$ groups. If the acyl chloride is not available, it is made from the corresponding acid and phosphorus pentachloride as is known in the art. It is preferred that the $R_{10}OH$, $(R_{10})_2O$, or $R_{10}Cl$ reactant does not have bulky, hindering substituents, e.g. tert-butyl, on both of the ring carbon atoms adjacent to the carbonyl attaching-site.

The formula-XXIX compound is next obtained by deiodination of XXVIII using a reagent which does not react with the lactone ring or the $OR_{10}$ moiety, e.g. zinc dust, sodium hydride, hydrazine-palladium, hydrogen and Raney nickel or platinum, and the like. Especially preferred is tributyltin hydride in benzene at about 25° C. with 2,2'-azobis(2-methylpropionitrile) as initiator.

The formula-XXX compound is obtained by demethylation of XXIX with a reagent that does not attack the $OR_{10}$ moiety, for example boron tribromide or trichloride. The reaction is carried out preferably in an inert solvent at about 0°–5° C.

The formula-XXXI compound is obtained by oxidation of the $-CH_2OH$ of XXX to $-CHO$, avoiding decomposition of the lactone ring. Useful for this purpose are dichromate-sulfuric acid, Jones reagent, lead tetraacetate, and the like. Especially preferred is Collins' reagent (pyridine-$CrO_3$) at about 0°–10° C.

The formula-XXXII compound is obtained by Wittig alkylation of XXXI, using the sodio derivative of the appropriate 2-oxoalkylphosphonate. The trans enone lactone is obtained stereospecifically (see D. H. Wadsworth et al., J. Org. Chem. Vol. 30, p. 680 (1965)).

In preparing the formula-XXXII compounds of Chart A, certain phosphonates are employed in the Wittig reaction. These are of the general formula

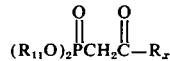

wherein $R_{11}$ is alkyl of one to 8 carbon atoms, inclusive, and $R_x$ has the same meaning as $R_x$ of Charts A-G, namely that $R_x$ is (1) alkyl of 2 to 4 carbon atoms, inclusive, substituted with zero to 2 fluoro, inclusive, (2) branched-chain alkyl of 5 carbon atoms or alkyl of 5 carbon atoms substituted with one or 2 fluoro, or (3) alkyl of 6 to 10 carbon atoms, inclusive, substituted with zero to 2 fluoro, inclusive. In preparing the preferred embodiments of this invention, phosphonates are used in which branching of fluoro substitution in $R_x$ is on the carbon atom adjacent to the carbonyl or on the carbon atom once-removed or on both of these carbon atoms, for example

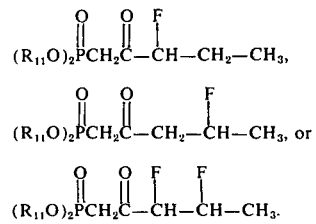

The phosphonates are prepared and used by methods known in the art. See Wadsworth et al., reference cited above. Conveniently, the appropriate aliphatic acid ester is condensed with dimethyl methylphosphonate in the presence of n-butyllithium. For this purpose, acids of the general formula $R_xCOOH$ are used in the form of their lower alkyl esters, preferably methyl or ethyl. For example methyl esters are formed from the acids by reaction with diazomethane. These aliphatic acids of various chain length, with or without branching or fluoro substitution within the scope of $R_x$ as defined above are known in the art or can be prepared by methods known in the art.

Aliphatic acids without branching or fluoro substitution are propionic, butyric, valeric, heptanoic, octanoic, nonanoic, decanoic, or undecanoic acids.

In the case of acids with branching, many are readily available, e.g. 2-methylpropionic, 2-methylbutyric, 2-ethylbutyric, 3-methylbutyric, 2,2-dimethylbutyric, 2-ethyl-2-methylbutyric, 2,2-dimethylbutyric, 2,3-dimethylbutyric, 3,3-dimethylbutyric, 2-methylvaleric, 2-propylvaleric, 3-methylvaleric, 2,2-dimethylvaleric, 3,3-diethylvaleric, 2-methyl-2-propylvaleric, 2-ethyl-3-methylvaleric, 2-methylhexanoic, 2-ethylhexanoic, 2-butylhexanoic, 2,2-dimethylhexanoic, 2,3-dimethylhexanoic, 2-butyl-2-methylhexanoic, 2-methylheptanoic, 2-propylheptanoic, 2-butylheptanoic, 2,2-diethylheptanoic, 2-methyl-2-propylheptanoic, 2-ethyloctanoic 2-propyloctanoic, 3-methyloctanoic, 2-ethyl-2-methyloctanoic, 2-ethylnonanoic, 2,2-dimethylnonanoic, and 2-methyldecanoic acid. Other acids are available by methods known in the art, for example reaction of a branched alkyl halide with sodium cyanide to form a nitrile and subsequent hydrolysis to the acid.

In the case of fluoro-substituted acids, many are readily available, e.g. 2-fluoropropionic, 3-fluoropropionic, 2,2-difluoropropionic, 2-fluorobutyric, 3-fluorobutyric, 2,2-difluorobutyric, 3,3-difluorobutyric, 2-fluorovaleric, 2-fluorohexanoic, 2-fluoroheptanoic, 2-fluorooctanoic, 2-fluorononanoic, and 2-fluorodecanoic acids. others are available by methods known in the art, for example by fluorination of 2-oxo or 3-oxo aliphatic acids with sulfur tetrafluoride to give 2,2-difluoro or 3,3-difluoro acids. For reactions of $SF_4$ see Martin et al., J. Org. Chem. 27, 3164 (1962). For other syntheses of fluorinated acids see Henne et al., J. Am. Chem. Soc. 69, 281 (1947). For fluorination of a ketone function with $MoF_6$. $BF_3$ see Mathey et al., Tetrahedron 27, 3965(1971). Other methods of synthesis include replacement of hydroxy by fluoro, see Ayer, U.S. Pat. 3,056,806; replacement of chloro or bromo by fluorine exchange with fluorides, or saturation of double bonds by fluorine atoms, see Advances in Fluorine Chemistry, M. Stacey et al. editors, Vol. 3, Butterworth and Co., 1963, especially pages 181–188. Thus, 2,3-difluoroundecanoic acid is prepared from 2-undecenoic acid either by saturating it using an inorganic fluoride such as lead fluoride, or by first forming 2,3-dibromoundecanoic acid and then replacing bromo with fluoro.

Continuing with Chart A, the formula-XXXIII compound is obtained as a mixture of alpha and beta isomers by reduction of XXXII. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane.

For production of natural-configuration PG-type compounds, the desired alpha form of the formula-XXXIII compound is separated from the beta isomer by silica gel chromatography.

The formula-XXXIV compound is then obtained by deacylation of XXXIII with an alkali metal carbonate, for example potassium carbonate in methanol at about 25° C.

The bis(tetrahydropyranyl) ether XXXV is obtained by reaction of the formula-XXXIV diol with dihydropyran in an inert solvent, e.g. dichloromethane, in the presence of an acid condensing agent such as p-toluenesulfonic acid or pyridine hydrochloride. The dihydropyran is used in excess, preferably 4 to 10 times theory. The reaction is normally complete in 15–30 min. at 20°–30° C.

The transformations of the formula-XXXVI compounds to the formula-XXXIX 4,5-didehydro $PGF_{1\alpha}$-type compounds are shown in Chart B.

The lactol XXXVI is obtained on reduction of the formula-XXXV lactone or its 15β epimer without reducing the 13,14-ethylenic group. For this purpose, diisobutyl-aluminum hydride is used. The reduction is preferably done at −60° to −70° C. The 15β-epimer corresponding to the formula-XXXV lactone is readily obtained by the steps of Chart A, using the 15β isomer of formula XXXIII.

Consider, next, step 1 of Chart B wherein the formula-XXXVI

CHART B

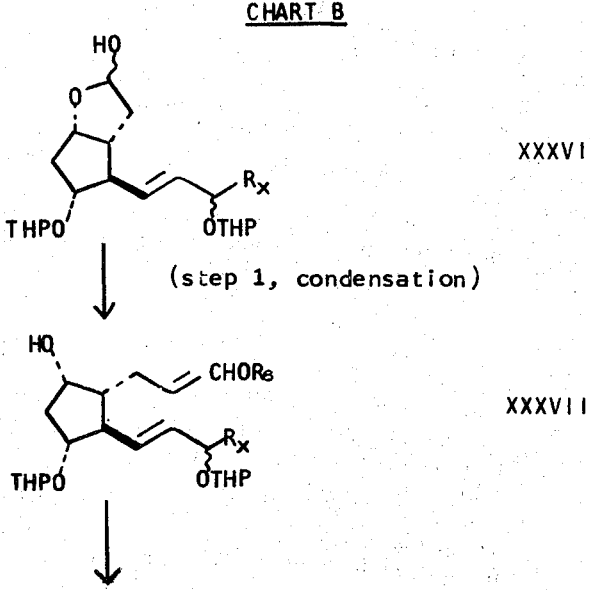

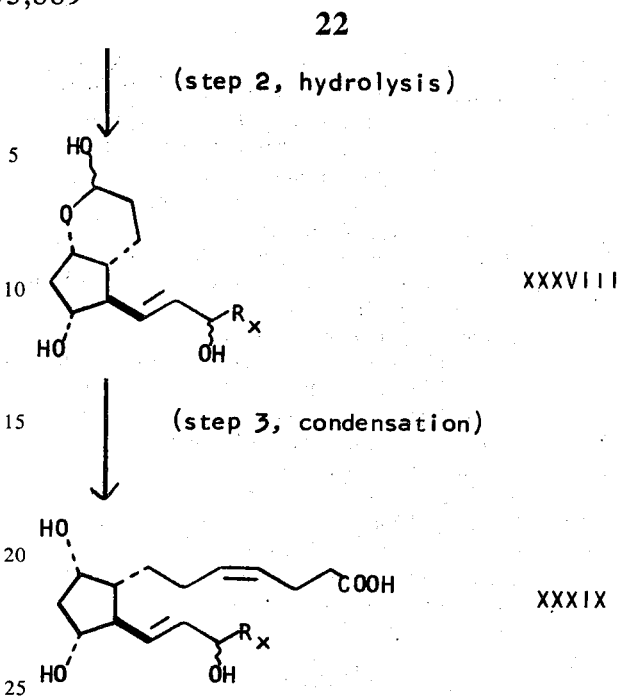

compounds undergo condensation to form the formula-XXXVII enol ethers. For this purpose, an alkoxymethylenetriphenylphosphorane is useful. See, for example, Levine, J. Am. Chem. Soc. 80, 6150 (1958). The reagent is conveniently prepared from a corresponding quaternary phosphonium halide and a base, e.g. butyl lithium or phenyl lithium, at a low temperature, e.g. preferably below −10°C. The formula-XXXVI lactol is mixed with the reagent and the condensation proceeds smoothly within the temperature range −30° C. to +30° C. At higher temperatures the reagent is unstable, whereas at low temperatures the rate of condensation is undesirably slow. Examples of the alkoxymethylenetriphenylphosphoranes preferred for forming the formula-XXXVII enol ethers are methoxy-, ethoxy-, propoxy-, isopropoxy-, butoxy-, isobutoxy-, sec-butoxy-, and tertbutoxymethylenetriphenylphosphorane.

Various hydrocarbyloxymethylenetriphenylphosphoranes which may be substituted for the alkoxymethylenetriphenylphosphoranes and are therefore useful for preparing formula-XXXVII intermediates wherein $R_6$ is hydrocarbyl, include alkoxy (of 1 to 4 carbon atoms)-, aralkoxy-, cycloalkoxy-, and aryloxymethylenetriphenylphosphoranes. Examples of these hydrocarbyloxymethylenetriphenylphosphoranes are 2-methylbutoxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropoxy-, cyclohexyloxy-, phenoxy-, and p-methylphenoxymethylenetriphenylphosphorane. See, for example, Organic Reactions, Vol. 14, pages 346–348, John Wiley and Sons, Inc., N.Y., (1965).

Consider, next, step 2 of Chart B, wherein the formula-XXXVII enol ether intermediates are hydrolyzed to the formula-XXXVIII lactols. This hydrolysis is done under acidic conditions, for example with perchloric acid or acetic acid. Tetrahydrofuran is a suitable diluent for this reaction mixture. Reaction temperatures of from 10° C. to 100° C. may be employed. The length of time required for hydrolysis is determined in part by the hydrolysis temperature. With acetic acid-water-tetrahydrofuran at about 60° C., several hours are sufficient.

Finally in step 3 of Chart B, the formula-XXXVIII lactols are transformed to the formula-XXXIX PGF-type products by condensation with a Wittig reagent derived from 3-carboxypropyltriphenylphosphonium halide and sodio methylsulfinylcarbanide. Dimethyl sulfoxide is conveniently used as a solvent, and the reaction may be done at about 25° C.

The various formula-XXXVII and -XXXVIII intermediates are useful directly as produced or they may be subjected to separation procedures, for example silica gel chromatography or recrystallization.

Reference to Chart C, herein, will make clear the transformation from the PGF-type compounds XL to the PGE-type compounds XLIII by steps 1–3, inclusive. Formulas XL, XLI, XLII, and XLIII, hereinafter referred to, are depicted in Chart C, wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_9$ is $R_1$ as defined above or silyl of the formula -Si-$(A)_3$ wherein A is as defined above; wherein $R_x$ is (1) alkyl of 2 to 4 carbon atoms, inclusive, substituted with zero to 2 fluoro, inclusive, (2) branched-chain alkyl of 5 carbon atoms or alkyl of 5 carbon atoms substituted with one or 2 fluoro, or (3) alkyl of 6 to 10 carbon atoms, inclusive, substituted with zero to 2 fluoro, inclusive; wherein E is trans $-CH=CH-$ or $-CH_2CH_2-$; and wherein $\sim$ indicates attachment of hydroxyl or silyl in alpha or beta configuration. The various A's of a -Si-$(A)_3$ moiety are alike or different. For example, an -Si-$(A)_3$ can be trimethylsilyl, dimethylpropylsilyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

Consider, then, step 1 of Chart C, wherein the formula-XL compounds are selectively silylated at the C-11 and C-15 positions, by choice of reagents and conditions. Silylating agents are known in the art. See, for example, Pierce, "Silylation of organic Compounds," Pierce Chemical Co., Rockford, Ill. (1968). Silylating agents of the type $(A)_3SiN(G)_2$, i.e. substituted silylamines wherein A is as defined above and G has the same definition as A, being the same or different, are useful for the above purpose at temperatures below about −25° C. A preferred temperature range is about −35° to =50°. At higher temperatures some silylation of C-9 hydroxyl groups as well as the C-11 and C-15 hydroxyl groups occurs, wherein at lower temperatures the rate of silylation is undesirably slow. Examples of silylamine type silylating agents suitable for forming the formula-XLI intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine,N,N,1,1-tetramethyl-1-phenylsilylamine, N,N-diethyl-1,1-dimethyl-1-phenylsilylamine, N,N-diethyl-1-methyl, 1,1-diphenylsilylamine, N,N-dibutyl-1,1,1-triphenyl-silylamine, and 1-methyl-N,N,1,1-tetraphenylsilylamine.

The reaction is carried out with exclusion of atmospheric moisture, for example under a nitrogen atmosphere. It is conveniently done in a solvent such as acetone or dichloromethane, although the silylating agent itself, when used in excess, may also serve as a liquid medium for the reaction. The reaction ordinarily is completed in a few hours, and should be terminated when the C-11 and C-15 hydroxyl groups are silylated, to avoid side reactions. The progress of the reaction is conveniently monitored by thinlayer chromatography (TLC), utilizing methods known in the art.

An excess of the reagent over that stoichiometrically required is used, preferably at least a four-fold excess. When $R_1$ in the formula-XL starting material is hydro-

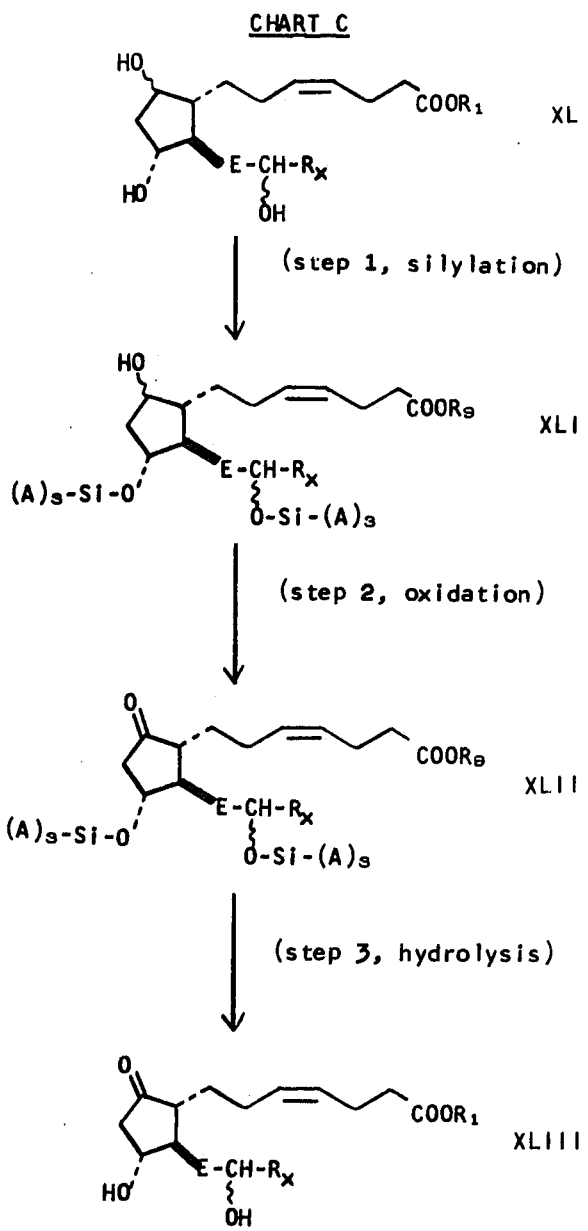

gen, the -COOH moiety thereby defined may be partially or even completely transformed to -COO-Si-(A)$_3$, additional silylating agent being used for this purpose. Whether or not this occurs is immaterial for the success of the process, since -COOH groups are not changed by the subsequent steps and -COO-Si-(A)$_3$ groups are easily hydrolyzed to -COOH groups.

Consider, next, step 2 of Chart C, wherein the formula XLI 11,15-disilyl ether intermediate is oxidized to compound XLII. Oxidation reagents useful for this transformation are known in the art. An especially useful reagent for this purpose is the Collins reagent, i.e. chromium trioxide in pyridine. See J.C. Collins et al., Tetrahedron Lett., 3363 (1968). Dichloromethane is a suitable diluent for this purpose. A slight excess of the oxidant beyond the amount necessary to oxidize the C-9 secondary hydroxy group of the formula-XLI intermediate is used. Reaction temperatures of below 20° C. should be used. Preferred reaction temperatures are in the range =10° to +10°C. The oxidation proceeds rapidly and is usually complete in about 5 to 20 minutes.

Finally in step 3 of Chart C, all silyl groups of the formula-XLII intermediates are removed by hydrolysis, thereby forming the formula-XLIII PGE-type products. These hydrolyses are carried out by prior art procedures known to be useful for transforming silyl ethers and silyl esters to alcohols and carboxylic acids, respectively. See, for example, Pierce, cited above, especially p. 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary. The formula-XLIII PGE-type product is isolated by conventional means.

The process of Chart C is also useful in transforming PGF-type compounds of formula XXV to the corresponding PGE-type compounds. Likewise, it is useful in transforming PGF-type compounds corresponding to formula XXI wherein R$_5$ is hydrogen and R$_x$ is replaced by n-pentyl.

Those PGF-type compounds of formulas IX, XIII, XVII, XXI, and XXVI wherein R$_5$ is methyl or ethyl are transformed to the corresponding PGE-type compounds by the steps shown in Chart D. Therein, formula XLIV is generic to those PkGF-type compounds named above. In Chart D, the symbols A, E, R$_1$, R$_9$, R$_x$, and ~ have the same meaning as in Chart C. M' represents either

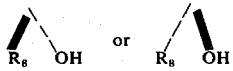

wherein R$_8$ is methyl or ethyl.

Following steps 1–3, which utilize essentially the same reagents and conditions as in steps 1–3 of Chart C, there are obtained the PGE-type compounds represented by formula XLVII. Under these conditions, the intermediates of formula XLV and XLVI are 11-silyl derivatives rather than the 11,15-disilyl derivatives of Chart C.

The novel 15-substituted PGF-type acids and esters of

CHART D

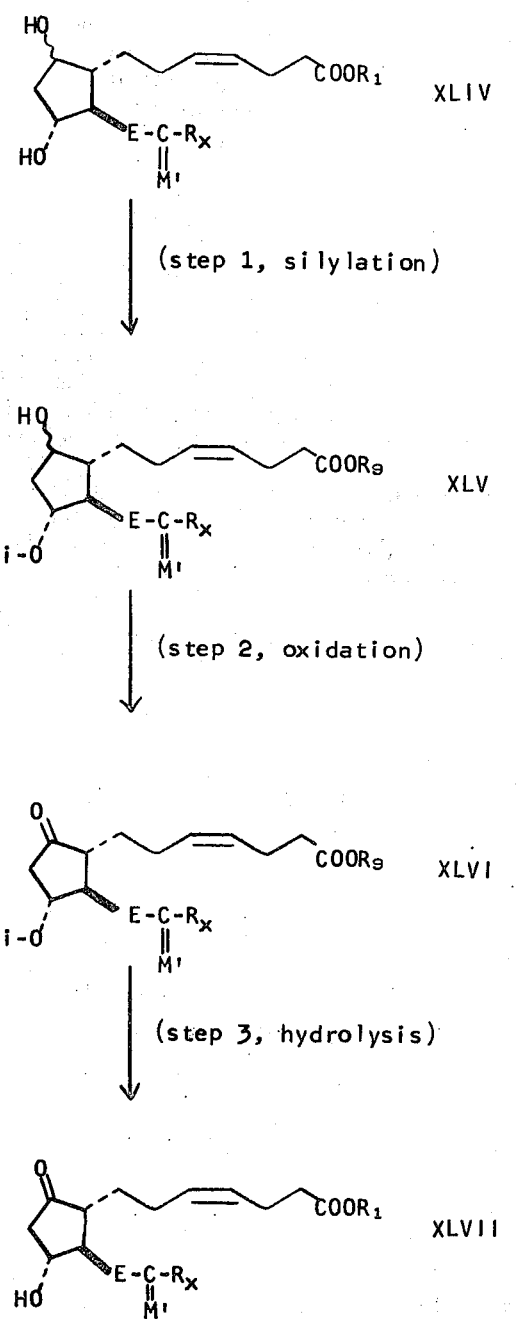

this invention represented by formulas IX, XIII, XVII, XXI, and XXVI wherein R$_5$ is methyl or ethyl are prepared by the sequence of transformations shown in Chart E, steps 1–3, inclusive. Formulas XLVIII, XLIX, L, LI, and LII, hereinafter referred to, are depicted in Chart E, wherein Q is

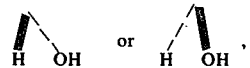

R$_8$ is methyl or ethyl, and A, E, R$_1$, R$_9$, R$_x$, and ~ are as defined for Chart C.

Consider, then, step 1 of Chart E, wherein the formula XLVIII PGF-type compounds are oxidized to the intermediate formula-XLIX 15-oxo acids and esters.

For this purpose, reagents such as 2,3-dichloro-5,6-dicyano-1,4-benzoquinone, activated manganese dioxide, or nickel peroxide are used, according to procedures known in the art. See Fieser et al., "Reagents for Organic Synthesis," John Wiley and Sons, Inc., New York, N.Y., (1967) pp. 215, 637, and 731.

Considering step 2 of Chart E, the formula-XLIX 15-oxo compounds are transformed to silyl derivatives of formula L by procedures known in the art. See, for example, Pierce, "Silylation of organic Compounds," Pierce Chemical Co., Rockford, Ill. (1968). Both hydroxy groups of the formula-XLIX reactants are thereby transformed to $-O-Si(A)_3$ moieties wherein A is as defined above, and sufficient of the silylating agent is used for that purpose according to known procedures. When $R_1$ in the formula-XLIX intermediate is hydrogen, the -COOH moiety thereby defined is simultaneously transformed to $-COO-Si(A)_3$, additional silylating agent being used for this purpose. This latter transformation is aided by excess silylating agent and prolonged treatment. When $R_1$ in formula XLIX is alkyl, then $R_9$ in formula L will also be alkyl. The necessary silylating

CHART E

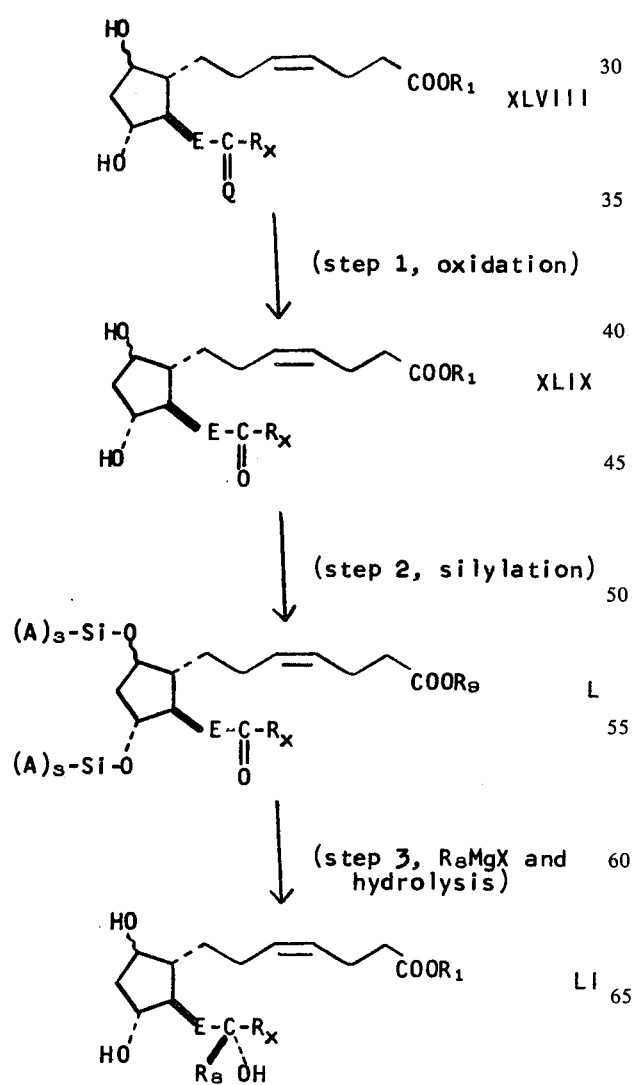

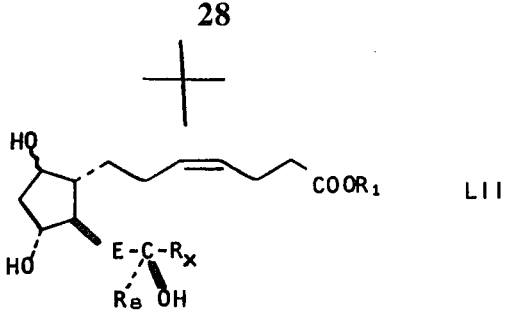

agents for these transformations are known in the art or are prepared by methods known in the art. See, for example, Post, "Silicones and Other organic Silicon Compounds," Reinhold Publishing Corp., New York, N.Y. (1949).

Considering step 3 of Chart E, the intermediate silyl compounds of formula L are transformed to the final 15-substituted compounds of formulas LI and LII by first reacting the silyl compound with a Grignard reagent of the formula $R_8MgHal$ wherein $R_8$ is as defined above, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl, trisilyl, or tetrasilyl tertiary alcohol is then hydrolyzed with water to remove the silyl groups. For this purpose, it is advantageous to use a mixture of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15-$\alpha$ and 15-$\beta$ isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15-$\alpha$ and 15-$\beta$ isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

The 15-substituted PGE-type compounds represented by formulas VIII, XII, XVI, XX, and XXVI are prepared from the above 15-substituted PGF-type compounds following the steps of Chart D, discussed above.

Chart F shows transformations from the formula LIII PGE-type compounds to the corresponding PGF-, PGA-, and PGB-type compounds. In figures LIII, LIV, LV, and LVI of Chart F, M is

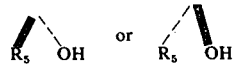

wherein $R_5$ is hydrogen, methyl, or ethyl; and E, $R_1$, $R_x$, and ~ are as defined above for Chart C.

Thus, the various PGF -type compounds encompassed by formulas IX, XIII, XVII, XXI, and XXVI wherein ~ is beta, are prepared by carbonyl reduction of the corresponding PGE type compounds, e.g. formulas VIII, XII, XVI, XX, and XXVI. For example, carbonyl reduction of 4,5-cis-didehydro-18,19,-20-trinor-PGE$_1$ gives a mixture of 4,5-cis-didehydro-18,19-20-trinor-PGF$_{1\alpha}$ and 4,5-cis-didehydro-18,19,20-trinor-PGF$_{1\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al, cited above, Granstrom et al., J. biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various PGA-type compounds encompassed by formulas X, XIV, XVIII, XXII, and XXVI are prepared

CHART F

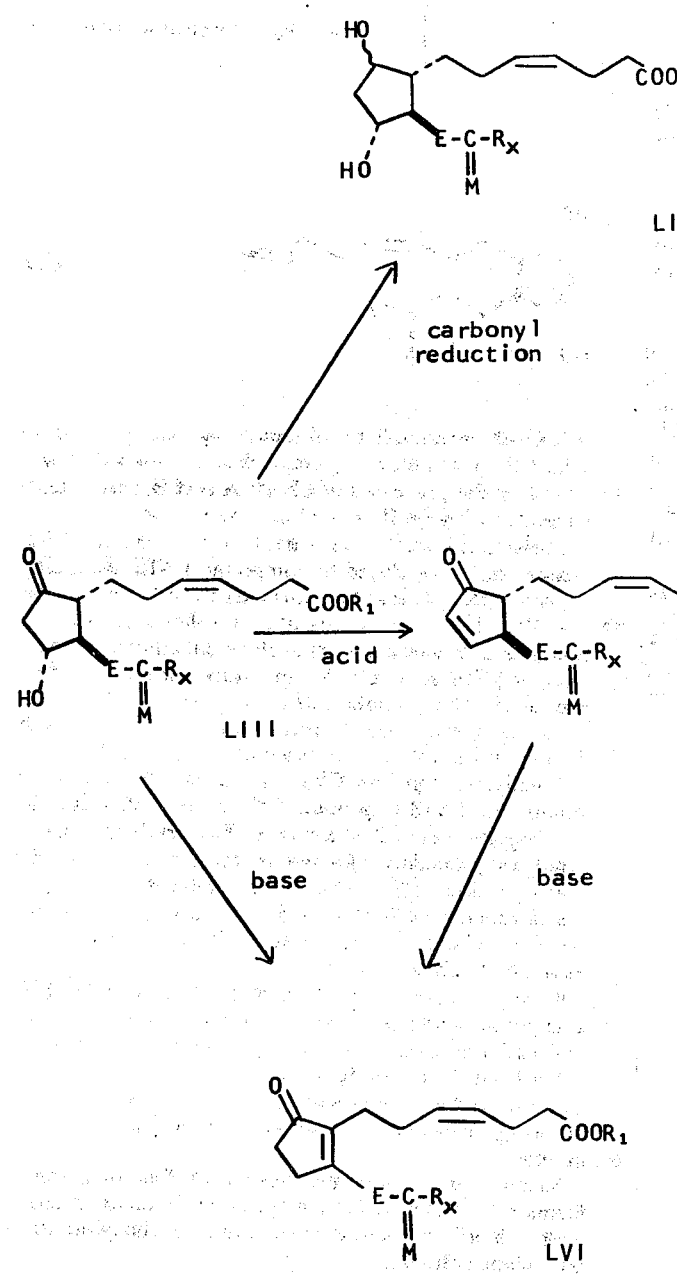

by acidic dehydration of the corresponding PGE-type compounds, e.g. formulas VIII, XII, XVI, XX, and XXVI. For example, acidic dehydration of 4,5-cis-didehydro-20-nor-PGE$_1$ gives 4,5-cis-didehydro-20-nor-PGA$_1$.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Pat. No. 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various PGB-type compounds encompassed by formulas XI, XV, XIX, XXIII, and XXVI are prepared by basic dehydration of the corresponding PGE-type compounds encompassed by formulas VIII, XII, XVI, XX, and XXVI or by contacting the corresponding PGA-type compounds encompassed by formulas X, XIV, XVII, XXII, and XXVI with base. For example, both 4,5-cis-didehydro-20-methyl-PGE$_1$ and 4,5-cis-didehydro-20methyl-PGA$_1$ give 4,5-cis-didehydro-20-methyl-PGB$_1$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 m$\mu$ for the PGB-type compound.

The 4,5-cis-didehydro-13,14-dihydro-PGF$_1$ -type compounds of formula XXVI are conveniently prepared by the process steps of Chart G. Therein, R$_7$ is alkyl of 2 to 10 carbon atoms, inclusive, substituted with zero to 2 fluoro, inclusive, and ~ indicates attachment of hydroxyl in alpha or beta configuration. When R$_7$ in the formula-LVII compound is R$_x$ as defined for Chart B, that compound is the formula

CHART G

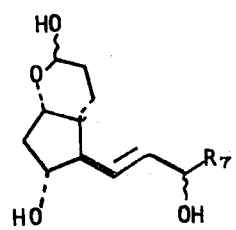

LVII (step 1, reduction)

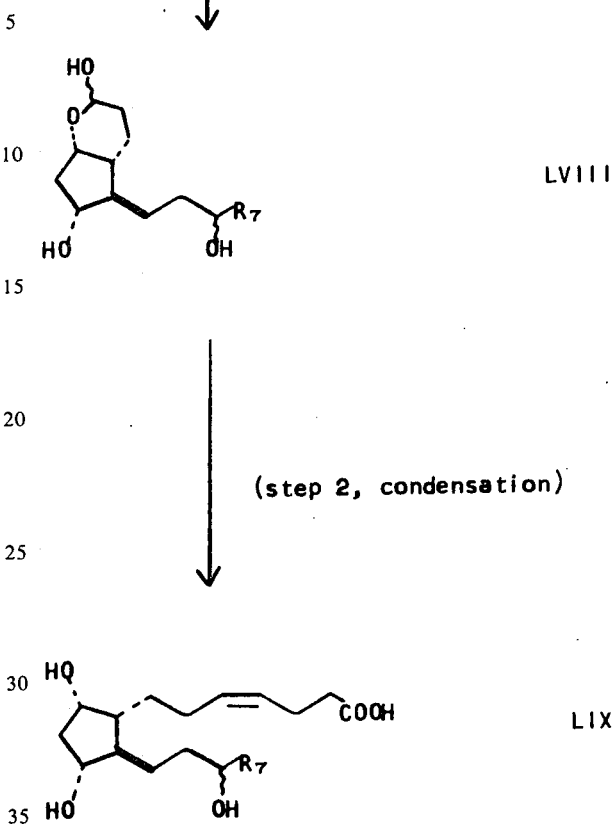

XXXVIII intermediate obtained by the process of Chart B. When R$_7$ is n-pentyl, that compound is prepared by the processes of Charts A and B, using intermediates wherein R$_x$ is replaced by n-pentyl.

Considering step 1 of Chart G, the formula-LVII intermediate is reduced to compound LVIII. Reducing agents useful for this transformation are known in the art. Thus, hydrogen is used at atmospheric pressure or low pressure with catalysts such as palladium on charcoal or platinum oxide. Temperatures of about 25° C. are used. The formula-LVIII compound is separated from starting material or other compounds by methods known in the art, e.g. silica gel chromatography.

Finally, in step 2 of Chart G, the transformation of compound LVIII to product LIX is done following the condensation step 3 of Chart B. The product is separated by procedures known in the art, for example silica gel chromatography or recrystallization.

Reference to Chart H will make clear the process steps by which 4,5-cis-didehydro-2a-homo-PGF$_1$ of Formula LXIII is formed.

In steps 1 and 2 of Chart H, first the formula-LX compound undergoes condensation to form the formula-LXI enol ether, and then, by hydrolysis, the formula-LXII lactol is formed. The formula-LX compound is obtained following the steps outlined in Chart A, using reagents and intermediates wherein R$_x$ is n-pentyl.

In step 3 of Chart H, the formula-LXII lactol is transformed to the formula-LXIII product by condensation with a Wittig reagent derived from 4-carboxybutyltriphenylphosphonium

CHART H

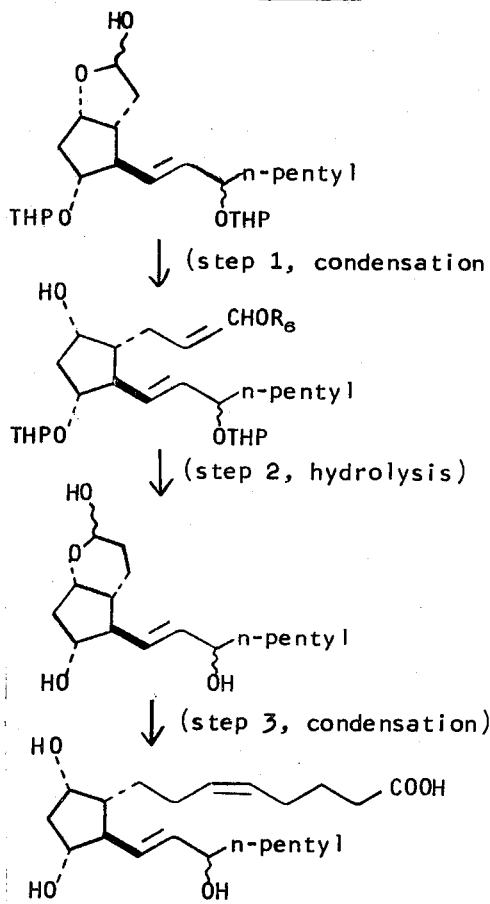

halide and sodio methylsulfinylcarbanide. Dimethyl sulfoxide is conveniently used as a solvent, and the reaction may be done at about 25° C. The product is separated by procedures known in the art, for example silica gel chromatography or recrystallization.

Optically active compounds are obtained from optically active intermediates according to the process steps of Chart A. Likewise, optically active products are obtained by the transformations of optically active compounds following the processes of Charts B, C, D, E, F, G, and H. When racemic intermediates are used in reactions corresponding to the processes of Charts A–H, inclusive, and racemic products are obtained, these racemic products may be used in their racemic form or, if preferred, they may be resolved as optically active isomers by procedures known in the art.

For example, when final compound VIII to XXVI is a free acid, the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula VIII to XXVI is then obtained by treatment of the salt with an acid by known general procedures.

As discussed above, the stereochemistry at C-15 is not altered by the transformations of Chart A; the 15β epimeric products of formula XXX are obtained from 15β formula-XXVII reactants. Another method of preparing the 15β products is by isomerization of the PGF$_1$- or PGE$_1$-type compounds having 15-α configuration, by methods known in the art. See, for example, Pike et al., J. Org. Chem. 34, 3552 (1969).

As discussed above, the processes of Charts B, C, D, E, F, G, and H lead variously to acids ($R_1$ is hydrogen) or to esters ($R_1$ is alkyl, cycloalkyl, aralkyl, phenyl or substituted phenyl, as defined above). When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol 8, pp. 389–394 (1954).

An alternative method for esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final formula VIII-to-XXVI compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula VIII-to-XXVI acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula VIII-to-XXVI acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VIII-to-XXVI acid with the stoichiometric amount of the corresponding quaternary ammonium hydroxide in water solution, followed by evaporation of the water.

The final formula VIII-to-XXVI acids or esters prepared by the processes of this invention are transformed to lower alkanoates by interaction of the formula VIII-to-XXVI hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure, the formula VIII, XII, XVI, XX, and XXVI PGE-type compounds are transformed to dialkanoates, the formula IX, XIII, XVII, XXI, XXV, and XXVI PGF-type compounds are transformed to trialkanoates, and the formula X, XIV, XVIII, XXII, and XXVI PGA-type and formula XI, XV, XIX, XXIII, and XXVI PGB-type compounds are transformed to monoalkanoates.

When a PGE-type dialkanoate is transformed to a PGF-type compound by carbonyl reduction as shown in Chart F, a PGF-type dialkanoate is formed and is used for the above-described purposes as such or is transformed to a trialkanoate by the above-described procedure. In the latter case, the third alkanoyloxy group can be the same as or different from the two alkanoyloxy groups present before the carbonyl reduction.

DESCRIPTION OF THE PREFERRED EMBODIMENTS

The invention can be more fully understood by the following examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

NMR spectra are recorded on a Varian A-60 spectrophotometer in deuterochloroform solutions with tetramethylsilane as an internal standard (downfield). "Brine", herein, refers to an aqueous saturated sodium chloride solution.

PREPARATION 1

3α-Benzoyloxy-5α-hydroxy-4-iodo-2β-methoxymethylcyclopentaneacetic Acid γ-Lactone (Formula XXVIII: $R_{10}$ is benzoyl).

Refer to Chart A. To a mixture of laevorotatory (-) iodolactone XXVII (E. J. Corey et al., J. Am. Chem. Soc. Vol. 92, p. 397 (1970), 75 g.) in 135 ml. of dry pyridine under a nitrogen atmosphere is added 30.4 ml. of benzoyl chloride with cooling to maintain the temperature at about 20°–40° C. Stirring is continued for an additional 30 min. About 250 ml. of toluene is added and the mixture concentrated under reduced pressure. The residue is dissolved in one 1. of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the title compound, m.p. 84°–86° C.; $[\alpha]_D$ + 7° ($CHCl_3$); infrared spectral absorptions at 1768, 1722, 1600, 1570, 1490, 1275, 1265, 1180, 1125, 1090, 1060, 1030, and 710 cm$^{-1}$; and NMR (nuclear magnetic resonance) peaks at 2.1–3.45, 3.3, 3.58, 4.38, 5.12, 5.51, 7.18–7.58, and 7.83–8.05 δ.

Following the procedure of Preparation 1, but replacing that optically active formula-XXVII iodolactone with the racemic compound of that formula and the mirror image thereof, there is obtained the corresponding racemic benzoxy compound.

Preparation 2

3α-Benzoyloxy-5α-hydroxy-2β-methoxy-methylcyclopentaneacetic Acid γ-Lactone (Formula XXIX: $R_{10}$ is benzoyl).

Refer to Chart A. To a solution of the optically active formula-XXVIII benzoxy compound (Preparation 1, 60 g.) in 240 ml. of dry benzene is added 2,2'-azobis-(2-methylpropionitrile) (approximately 60 mg.). The mixture is cooled to 15° C. and to it is added a solution of 75 g. tributyltin hydride in 600 ml. of ether, with stirring, at such a rate as to maintain continuous reaction at about 25° C. When the reaction is complete as shown by TLC (thin layer chromatography) the mixture is concentrated under reduced pressure to an oil. The oil is mixed with 600 ml. of Skellysolve B (mixture of isomeric hexanes) and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product, is separated, dried over magnesium sulfate, and concentrated under reduced pressure to an oil, 39 g. of the title compound. An analytical sample gives [α]$_D$ —99° (CHCl$_3$); infrared spectral absorptions at 1775, 1715, 1600, 1585, 1490, 1315, 1275, 1180, 1110, 1070, 1055, 1025, and 715 cm$^{-1}$.; NMR peaks at 215-3.0, 3.25, 3.34, 4.84–5.17, 5.17–5.4, 7.1–7.5, and 7.8–8.05 δ; and mass spectral peaks at 290, 168, 105, and 77.

Following the procedure of Preparation 2, the racemic benzoxy compound following Preparation 1 is transformed to the corresponding racemic lactone.

PREPARATION 3

3α-Benzoyloxy-5α-hydroxy-2β-hydroxy-methylcyclopentaneacetic Acid γ-Lactone (Formula XXX: R$_{10}$ is benzoyl).

Refer to Chart A. To a cold (0°–5° C.) solution of lactone XXIX (Preparation 2, 20 g.) in 320 ml. of dichloromethane under nitrogen is added a solution of 24.8 ml. of boron tribromide in 320 ml. of dichloromethane, dropwise with vigorous stirring over a period of 50 min. at 0°–5° C. Stirring and cooling are continued for 1 hr. When the reaction is complete, as shown by TLC, there is cautiously added a solution of sodium carbonate (78 G. monohydrate) in 200 ml. of water. The mixture is stirred at 0°–5° C. for 10–15 min., saturated with sodium chloride, and the ethyl acetate layer separated. Additional ethyl acetate extractions of the water layer are combined with the main ethyl acetate solution. The combined solutions are rinsed with brine, dried over sodium sulfate and concentrated under reduced pressure to an oil, 18.1 g. of the title compound. An analytical sample has m.p. 116°–118° C.; [α]$_D$ —80° (CHCl$_3$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0 δ.

Following the procedure of Preparation 3, the racemic lactone following Preparation 2 is transformed to the corresponding racemic hydroxymethyl compound.

PREPARATION 4

3α-Benzoyloxy-2β-carboxaldehyde-5α-hydroxycyclopentaneacetic Acid γ-Lactone (Formula XXXI: R$_{10}$ is benzoyl).

Refer to Chart A. To a mixture of 150 ml. of dry dichloromethane and Collins' reagent J. C. Collins et al, Tetrahedron Lett. 3363 (1968), 28 g.) at about 10° C. under nitrogen is added, with vigorous stirring, a cold (10° C.) solution of the optically active hydroxymethyl lactone XXX (Preparation 3, 5.0 g.) in 150 ml. of dichloromethane. After 5-min. additional stirring, about 100 ml. of dry benzene is added, the mixture is filtered, and the solution is concentrated under reduced pressure. The volume is brought to about 150 ml. with benzene. The solution of the formula-XXXI title compound is used directly.

From a similar run, there is obtained by concentration of the benzene solution under reduced pressure an oil which, on trituration with ether, yields crystals of the optically active formula-XXXI compound, m.p. 115° C. (dec); and having NMR peaks at 1.8–3.7, 4.9–5.2, 5.54–5.77, 7.2–7.6, 7.7–8.0, and 9.8 δ.

Following the procedure of Preparation 4, the racemic hydroxymethyl compound following Preparation 3 is transformed to the corresponding racemic aldehyde.

PREPARATION 5 dl-Dimethyl 2-Oxo-3-methylheptylphosphonate,

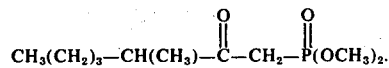

n-Butyllithium (150 ml.) is slowly added to a solution of dimethyl methylphosphonate (25.6 g.) in 475 ml. of tetrahydrofuran (THF) at about —65° C. To the mixture is added a solution of racemic ethyl 2-methylhexanoate (18.4 g.) in 50 ml. of THF, and the resulting mixture is stirred at —70° C. for 2 hrs. Then, 16 ml. of acetic acid is added, and the mixture is concentrated under reduced pressure. The residue is mixed with dichloromethane (about 400 ml.) and water (about 50 ml.), shaken, and separated. The organic phase is dried over magnesium sulfate and concentrated. Distillation yields the title compound, 16.7 g., b.p. 126°–129° C./1 mm.

Following the procedure of Preparation 5 but replacing racemic ethyl 2-methylhexanoate with the ethyl esters of the (+) and (—) isomers of 2-methylhexanoic acid (see P. A. Levene et al., J. Biol. Chem. 70, 211 (1926) and 84, 571 (1929)) there are obtained the corresponding optically active (+) and (—) title compounds.

Likewise following the procedure of Preparation 5, but replacing racemic ethyl 2-methylhexanoate with each of the following aliphatic acid esters there are obtained the corresponding phosphonates, with optically active esters yielding optically active phosphonates and racemic esters yielding racemic phosphonates:

methyl propionate
ethyl butyrate
methyl valerate
ethyl heptanoate
ethyl octanoate
methyl nonanoate
methyl decanoate
ethyl undecanoate
ethyl 2-methylpropionate
methyl 2-ethylbutyrate
methyl 2,2-dimethylbutyrate
ethyl 2,2-dimethylhexanoate
methyl 2,3-dimethylhexanoate
methyl 2-ethylhexanoate
ethyl 2-butylhexanoate
ethyl 2-ethyl-2-methyloctanoate
methyl 2-ethylnonanoate
ethyl 2-methyldecanoate
methyl 2-fluoropropionate
ethyl 3-fluoropropionate
ethyl 2,2-difluoropropionate
methyl 2-fluorobutyrate
ethyl 3,3-difluorobutyrate
ethyl 2-fluorovalerate
methyl 2-fluorohexanoate
methyl 2,2-difluorohexanoate
ethyl 2-fluoroheptanoate
methyl 2-fluorooctanoate
methyl 2-fluorodecanoate For example, ethyl butyrate yields dimethyl 2-oxopentylphosphonate; racemic methyl 2-ethylhexanoate yields racemic dimethyl 2-oxo-3-ethylheptylphosphonate; and optically active methyl 2-fluorodecanoate yields optically active dimethyl 2-oxo-3-fluoroundecylphosphonate.

PREPARATION 6

3α-Benzoyloxy-5α-hydroxy-2β-(3-oxo-4-methyl-trans-1-octenyl)-1α-cyclopentaneacetic Acid γ-Lactone (Formula XXXII: $R_x$ is 1-methylpentyl and $R_{10}$ is benzoyl).

Refer to Chart A. A solution of racemic dimethyl 2-oxo-3-methylheptylphosphonate (Preparation 5, 7.9 g.) in 36 ml. of THF is added, with stirring, to a cold (5° C.) suspension of sodium hydride (55%, 1.62 g.) in 180 ml. of THF. Thereafter the reaction mixture is stirred at about 25° C. for 2.5 hrs., and cooled to −10° C. To the mixture is added a benzene solution of optically active aldehyde XXXI (Preparation 4, 108 ml.). After 1.5 hrs., 1.8 ml. of acetic acid is added and the THF distilled under vacuum. The residue is dissolved in ethyl acetate and the solution is washed with brine, dried over sodium sulfate, and concentrated under reduced pressure. Chromatography over silica gel using 25–30% ethyl acetate in Skellysolve B (isomeric hexanes) for elution yields the separated diastereomers, i.e. C-16 epimers of the formula-XXXII title compound.

Following the procedure of Preparation 6, again using the optically active aldehyde XXXI, but replacing the racemic phosphonate with each of the optically active (+) and (−) 2-oxo-3-methylheptylphosphonates following Preparation 5, there are obtained the corresponding optically active formula-XXXII compounds.

Following the procedure of Preparation 6, but replacing aldehyde XXXI with the racemic aldehyde disclosed following Preparation 4, and using each of the phosphonates of and following Preparation 5, there are obtained the ketones corresponding to the formula-XXXII compounds.

The racemic aldehydes, when reacted with a racemic phosphonate, each yield two pairs of racemates which are separable into separate pairs of racemic compounds by methods known in the art, e.g. silica gel chromatography. The racemic aldehydes, when reacted with an optically active phosphonate, each yield a pair of diastereomers, which are separable, e.g. by silica gel chromatography.

Following the procedure of Preparation 6, optically active aldehyde XXXI yields, with dimethyl 2-oxopentylphosphonate, optically active ketone XXXII wherein $R_x$ is propyl. Optically active aldehyde XXXI yields, with racemic dimethyl 2-oxo-3-ethylheptylphosphonate, the diastereomeric ketones corresponding to formula XXXII wherein $R_x$ is 1-ethylpentyl. Racemic aldehyde XXXI yields, with optically active dimethyl 2-oxo-3-fluoroundecylphosphonate, diastereomeric ketones corresponding to formula XXXII wherein $R_x$ is 1-fluorononyl.

PREPARATION 7

3α-Benzoyloxy-5α-hydroxy-2β-(3α-hydroxy-4-methyl-trans-1-octenyl)-1α-cyclopentane-acetic Acid γ-Lactone (Formula XXXIII: $R_x$ is 1-methylpentyl, $R_{10}$ is benzoyl, and ~ is alpha).

Refer to Chart A. A solution containing the 16-epimers of ketone XXXII (Preparation 6, 2.75 g.) in 14 ml. of 1,2-dimethoxyethane is added to a mixture of zinc borohydride prepared from zinc chloride (anhydrous, 4.94 g.) and sodium borohydride (1.12 g.) in 48 ml. of dry 1,2-dimethoxyethane, with stirring and cooling to −10° C. Stirring is continued for 2 hrs. at 0° C., and water (7.8 ml.) is cautiously added, followed by 52 ml. of ethyl acetate. The mixture is filtered, and the filtrate is separated. The ethyl acetate solution is washed with brine, dried over sodium sulfate, and concentrated under reduced pressure to a mixture of the corresponding formula-XXXIII 15-alpha and 15-beta isomers. The compounds are subjected to chromatography on a silica gel column, eluting with ethyl acetate, to separate the 15-alpha (less polar) and 15-beta isomers of the C-16 epimers of the formula-XXXIII title compounds.

Following the procedure of Preparation 7, the ketones derived from the various phosphonates following Preparation 6 are transformed to the optically active or racemic hydroxy compounds corresponding to formula XXXIII, wherein $R_{10}$ is benzoyl. Thus, for example, there are obtained the hydroxy compounds wherein $R_x$ is propyl, 1-ethylpentyl, or 1-fluorononyl.

PREPARATION 8

3α,5α-Dihydroxy-2β-(3α-hydroxy-4-methyl-trans-1-octenyl)-1α-cyclopentaneacetic Acid γ-Lactone (Formula XXXIV: $R_x$ is 1-methylpentyl).

Refer to Chart A. Potassium carbonate (0.79 g.) is added to a solution of the mixed C-16 alpha and beta epimeric alpha-hydroxy formula-XXXIII compounds (Preparation 7, 2.2 g.) in 25 ml. of methanol, and the mixture is stirred for 1 hr. at about 25° C. Thereafter, 80 ml. of chloroform is added, the mixture is filtered, and the organic phase is concentrated under reduced pressure. The residue is taken up in dichloromethane and the solution washed with brine. Concentration of the organic phase gives a residue which is triturated with Skellysolve B, then concentrated to the corresponding mixed C-16 alpha and beta epimeric 15-alpha formula-XXXIV title compounds, 1.2 g.

Following the procedure of Preparation 8, each of the optically active or racemic hydroxy compounds corresponding to Formula XXXIII described following Preparation 7, is transformed to the corresponding optically active or racemic compound corresponding to formula XXXIV. Thus, for example, there are obtained the compounds wherein $R_x$ is propyl, 1-ethylpentyl, or 1-fluorononyl.

PREPARATION 9

3α,5α-Dihydroxy-2β-(3α-hydroxy-4-methyl-trans-1-octenyl)-1α-cyclopentaneacetic Acid γ-Lactone, 3,3′-Bis(tetrahydropyranyl) Ether (Formula XXXV: $R_x$ is 1-methylpentyl).

Refer to Chart A. A solution of the formula-XXXIV diols (Preparation 8, 1.3 g.), 4.25 ml. of dihydropyran, and 0.019 g. of p-toluenesulfonic acid in 35 ml. of dichloromethane is stirred at about 25° C. for 30 min. The solution is washed with potassium bicarbonate solution, dried, and concentrated under reduced pressure to yield the formula-XXXV title compound, 2.7 g.

Following the procedures of Preparation 9, each of the optically active or racemic compounds corresponding to formula XXXIV described following Preparation 8 is transformed to an optically active or racemic compounds corresponding to formula XXXV, for example' wherein $R_x$ is propyl, 1-ethylpentyl, or 1-fluorononyl.

PREPARATION 10

3α,5α-Dihydroxy-2β-(3α-hydroxy-4-methyl-trans-1-octenyl)-1α-cyclopentaneacetaldehyde γ-Lactol, 3,3'-Bis(tetrahydropyranyl) Ether (Formula XXXVI: $R_x$ is 1-methyl-pentyl and ~ is alpha or beta).

Refer to Chart B. Diisobutylaluminum hydride (2.6 ml.) in 25 ml. of toluene is added dropwise to a stirred solution of the formula-XXXV tetrahydropyranyl ether (Preparation 9, 2.7 g.) in 30 ml. of toluene cooled to −70° C. Stirring is continued at −70° C. for 30 min., whereupon a solution of 12 ml. of THF and 6 ml. of water is cautiously added. The mixture is filtered and the filtrate is washed with brine, dried, and concentrated to the mixed alpha and beta hydroxy isomers of the formula-XXXVI title compounds, 2.4 g., showing no lactone absorption in their infrared spectra.

Following the procedures of Preparation 10, each of the optically active or racemic compounds corresponding to formula XXXV described following Preparation 9 is transformed to the corresponding optically active or racemic compound corresponding to formula XXXVI, for example, wherein $R_x$ is propyl, 1-ethylpentyl, or 1-fluorononyl.

PREPARATION 11

3α,5α-Dihydroxy-2β-(3α-hydroxy-trans-1-octenyl)-1α-cyclopentanepropionaldehyde δ-Lactol (Formula LXII: ~OH is alpha).

1. Refer to Chart H. A suspension of methoxymethyltriphenylphosphonium chloride (Levine, J. Am. Chem. Soc. 80, 6150 (1958), 32.4 g.) in 150 ml. of tetrahydrofuran (THF) is cooled to −15° C. and to it is added 69.4 ml. of butyllithium (1.6 M. in hexane) in 45 ml. of THF. After 30 min. there is added a solution of the formula-XXXVI 3α,5α-dihydroxy-2β-(3α-hydroxy-trans-1-octenyl)-1α-cyclopentaneacetaldehyde γ-lactol bis(tetrahydropyranyl) ether (Corey et al., J. Am. Chem. Soc. 92, 397 (1970), 10.0 g.) in 90 ml. of THF. The mixture is stirred for 1.5 hrs., meanwhile warming to about 25° C., and is then concentrated under reduced pressure. The residue is partitioned between dichloromethane and water, and the organic phase is dried and concentrated. This residue is then subjected to chromatography over silica gel, eluting with cyclohexane-ethyl acetate (2:1). Those fractions shown by thin-layer chromatography (TLC) to contain the formula-LXI intermediate are combined and concentrated to yield that enol-ether, 5.2 g.

2. The above enol-ether, in 20 ml. of THF, is hydrolyzed with 50 ml. of 66% acetic acid at about 57° C. for 2.5 hrs. The mixture is concentrated under reduced pressure. Toluene is added to the residue and the solution is again concentrated. Finally the residue is subjected to chromatography on silica gel, eluting with chloroform-methanol (6:1). The title compound is obtained by combining and concentrating suitable fractions, 2.54 g.; recrystallized from ethyl acetate, m.p. 121°–123° C., infrared absorption at 3500, 1315, 1220, 1140, 1120, 1045, 1020, and 970 cm$^{-1}$.

Following the procedures of Preparation 11, but replacing the formula XXXVI compound with the corresponding 3β-hydroxy ether compound there is obtained the corresponding formula-XXXVIII 3β-hydroxy compound, namely 3α,5α-dihydroxy-2β-(3β-hydroxy-trans-1-octenyl)-1α-cyclopentanepropionaldehyde δ-lactol. Likewise, the racemic 3α- or 3β-hydroxy ether compounds yield the corresponding racemic 3α- or 3β-hydroxy δ-lactols.

EXAMPLE 1

3α,5α-Dihydroxy-2β-(3α-hydroxy-4-methyl-trans-1-octenyl)-1α-cyclopentanepropionaldehyde δ-Lactol (Formula XXXVIII: $R_x$ is 1-methylpentyl and ~OH is alpha).

Refer to Chart B. A suspension of methoxymethyltriphenylphosphonium chloride (Levine, J. Am. Chem. Soc. 80, 6150 (1958), 32.4 g.) in 150 ml. of tetrahydrofuran (THF) is cooled to −15° C. and to it is added 69.4 ml. of butyllithium (1.6 M. in hexane) in 45 ml. of THF. After 30 min. there is added a solution of the formula-XXXVI 3α,5α-dihydroxy-2β-(3α-hydroxy-4-methyl-trans-1-octenyl)-1α-cyclopentaneacetaldehyde γ-lactol bis(tetrahydropyranyl) ether (Preparation 10, 10.0 g.) in 90 ml. of THF. The mixture is stirred for 1.5 hrs., meanwhile warming to about 25° C., and is then concentrated under reduced pressure. The residue is partitioned between dichloromethane and water, and the organic phase is dried and concentrated. This residue is then subjected to chromatography over silica gel, eluting with cyclohexane-ethyl acetate (2:1). Those fractions shown by thin-layer chromatography (TLC) to contain the formula-XXXVII intermediate are combined and concentrated to yield that enol-ether.

The above enol-ether, in 20 ml. of THF, is hydrolyzed with 50 ml. of 66% acetic acid at about 57° C. for 2.5 hrs. The mixture is concentrated under reduced pressure. Toluene is added to the residue and the solution is again concentrated. Finally the residue is subjected to chromatography on silica gel, eluting with chloroform-methanol (6:1). The title compound is obtained by combining and concentrating suitable fractions.

Following the procedures of Example 1, but replacing the formula-XXXVI compound with the corresponding racemic 3α,5α-dihydroxy-2β-(3α-hydroxy-4-methyl-trans-1-octenyl)-1α-cyclopentaneacetaldehyde γ lactol bis(tetrahydropyranyl) ether obtained following Preparation 10, there is obtained the corresponding racemic δ-lactol, namely, dl-3α,5α-dihydroxy-2β-(3α-hydroxy-4-methyl-trans-1-octenyl)-1α-cyclopentanepropionaldehyde δ-lactol.

Following the procedures of Example 1, but replacing the formula-XXXVI compound with the corresponding optically active 3β-hydroxy ether compound, there is obtained the corresponding optically active formula-XXXVIII 3β-hydroxy compound, namely 3α,5α-dihydroxy-2β-(3β-hydroxy-4-methyl-trans-1-octenyl)-1α-cyclopentanepropionaldehyde δ-lactol.

Following the procedures of Example 1, but replacing the formulaL-XXXVI compound with the corresponding racemic 3β-hydroxy ether compound, there is obtained the corresponding racemic 3β-hydroxy δ-lactol, namely dl-3α,5α-dihydroxy-2β-(3β-hydroxy-trans-1-octenyl)-1α-cyclopentanepropionaldehyde δ-lactol.

Likewise following the procedures of Example 1, but replacing the formula-XXXVI compound with the various optically active or racemic 3α- or 3β-hydroxy ether compounds obtained following Preparation 10, for example wherein $R_x$ is propyl, 1-ethylpentyl, or 1-fluorononyl, there is obtained the corresponding optically active or racemic 3α- or 3β-hydroxy propionaldehyde δ-lactol corresponding to formula XXXVIII.

EXAMPLE 2

4,5-cis-Didehydro-16-methyl-PGF$_{1\alpha}$ (Formula IX: R$_1$ and R$_5$ are hydrogen, R$_x$ is 1-methylpentyl, and ~ is alpha).

Refer to Chart B. 3-Carboxypropyltriphenylphosphonium bromide is prepared by heating triphenylphosphine (156.8 g.) and 4-bromobutyric acid (100 g.) in 125 ml. of benzene at reflux for 18 hrs. The crystalline product is filtered off, washed with benzene, and recrystallized from ethanolacetonitrile-ether, 150 g., m.p. 247°–249° C.

The above phosphonium bromide (10.6 g.) is added to sodio methylsulfinylcarbanide prepared from sodium hydride (2.08 g., 57%) and 30 ml. of dimethyl sulfoxide, and the resulting Wittig reagent is combined with the formula-XXXVIII lactol of Example 1, in 20 ml. of dimethyl sulfoxide. The mixture is stirred overnight, diluted with about 200 ml. of benzene, and washed with potassium hydrogen sulfate solution. The two lower layers are washed with dichloromethane, and the organic phases are combined, washed with brine, dried, and concentrated under reduced pressure. The residue is subjected to chromatography over acid-washed silica gel, eluting with ethyl acetate-isomeric hexanes (3:1). Those fractions shown to contain the desired compound by TLC are combined and concentrated to yield the title compound.

Following the procedures of Example 2, but replacing the formula-XXXVIII lactol of that Example with the corresponding formula-XXXVIII 3β-hydroxy compound obtained following Example 1, there is obtained the corresponding formula-XXXIX 4,5-cis-didehydro-15β-PGF$_{1\alpha}$ product, corresponding to formula XVII wherein R$_1$ and R$_5$ are hydrogen, R$_4$ is 1-methylpentyl, and ~ is alpha.

Following the procedures of Example 2, but replacing the formula-XXXVIII lactol with the corresponding racemic 3α- or 3β-hydroxy lactol obtained following Example 1, there is obtained the corresponding dl-4,5-cis-didehydro-16-methyl-PGF$_{1\alpha}$ or dl-4,5-cis-didehydro-16-methyl-15β-PGF$_{1\alpha}$ product.

Likewise following the procedures of Example 2, but replacing the formula-XXXVIII lactol with the various optically active or racemic 3α- or 3β-hydroxy lactols obtained following Example 1, for example, wherein R$_x$ is propyl 1-ethylpentyl, or 1-fluorononyl, there is obtained the corresponding optically active or racemic 4,5-cis-didehydro-PGF$_1$ or 4,5-cis-didehydro-15β-PGF$_{1\alpha}$ type product, within the scope of formulas IX and XVII, for example:

4,5-cis-didehydro-19,20-dinor-PGF$_{1\alpha}$
dl-4,5-cis-didehydro-19,20-dinor-PGF$_{1\alpha}$
4,5-cis-didehydro-19,20-dinor-15β-PGF$_{1\alpha}$
dl-4,5-cis-didehydro-19,20-dinor-15β-PGF$_{1\alpha}$
4,5-cis-didehydro-16-ethyl-PGF$_{1\alpha}$
dl-4,5-cis-didehydro-16-ethyl-PGF$_{1\alpha}$
4,5-cis-didehydro-16-ethyl-15β-PGF$_{1\alpha}$
dl-4,5-cis-didehydro-16-ethyl-15β-PGF$_{1\alpha}$
4,5-cis-didehydro-16-fluoro-20-butyl-PGF$_{1\alpha}$
dl-4,5-cis-didehydro-16-fluoro-20-butyl-PGF$_{1\alpha}$
4,5-cis-didehydro-16-fluoro-20-butyl-15β-PGF$_{1\alpha}$
dl-4,5-cis-didehydro-16-fluoro-20-butyl-15β-PGF$_{1\alpha}$

EXAMPLE 3

4,5-cis-Didehydro-16-methyl-PGF$_{1\alpha}$, Methyl Ester (Formula IX: R$_1$ is methyl, R$_5$ is hydrogen, R$_x$ is 1-methylpentyl, and ~ is alpha).

A solution of diazomethane (about 50% excess) in diethyl ether (25 ml.) is added to a solution of 4,5-cis-didehydro-16-methyl-PGF$_{1\alpha}$ (Example 2, 50 mg.) in 25 ml. of a mixture of methanol and diethyl ether (1:1). The mixture is left standing at 25° C. for 5 min. and then is concentrated under reduced pressure to the title compound.

Following the procedure of Example 3, each of the 4,5-cis-didehydro-PGF$_{1\alpha}$ type products obtained following Example 2, including their 15β-epimers and the racemic forms, is transformed to a corresponding methyl ester.

EXAMPLE 4

4,5-cis-Didehydro-16-methyl-PGE$_1$, Methyl Ester (Formula VIII: R$_1$ is methyl, R$_5$ is hydrogen, R$_x$ is 1-methylpentyl, and ~ is alpha).

Refer to Chart C. 1. A solution of 4,5-cis-didehydro-16-methyl-PGF$_{1\alpha}$, methyl ester (Example 3, 480 mg.) in 20 ml. of acetone is cooled to about −50° C. and to it is added 4 ml. of N-trimethylsilyldiethylamine. The mixture is kept under nitrogen at −50° C. for 2.5 hrs. Progress of the reaction is monitored by TLC. The reaction mixture is diluted with about 200 ml. of diethyl ether. The solution is washed with about 150 ml. of cold brine and cold saturated potassium bicarbonate solutions. The ether extract is concentrated to a residue containing 4,5-cis-didehydro-16-methyl-PGF$_{1\alpha}$, 11,15-bis(trimethylsilyl) ether, methyl ester (Formula XLI).

2. For the oxidation step, a solution of the above 11,15-bis(trimethylsilyl) ether in dichloromethane (4 ml.) is added to a solution of CrO$_3$-pyridine (prepared from 0.26 g. of CrO$_3$ and 0.4 ml. of pyridine in 16 ml. of dichloromethane). The mixture is stirred for 5 min. at about 0° C. and 5 min. at about 25° C., then diluted with 10 ml. of ethyl acetate and filtered through silica gel. The solution, together with rinsings, is concentrated under reduced pressure to yield the formula-XLII compound.

3. The product of step 2 is hydrolyzed in 6 ml. of methanol, 1 ml. of water, and about 0.1 ml. of acetic acid at about 35° C. for 15 min. The volatiles are removed under reduced pressure and the residue is partitioned between dichloromethane and water. The organic phase is separated, dried over sodium sulfate, and concentrated under reduced pressure. The residue is chromatographed on silica gel, eluting with ethyl acetate-Skellysolve B (isomeric hexanes) (4:1). Those fractions containing the title compound free of starting material and impurities are combined and concentrated to yield the title compound.

Following the procedures of Example 4, but replacing 4,5-cis-didehydro-16-methyl-PGF$_{1\alpha}$, methyl ester, with 4,5-cis-didehydro-16-methyl-15β-PGF$_{1\alpha}$ obtained following Example 2, there is obtained the formula-XVI 4,5-cis-didehydro-16-methyl-15β-PGE$_1$ product. Similarly, the corresponding racemic PGF$_{1\alpha}$ type compounds yield the corresponding racemic PGE$_1$ type products.

Likewise following the procedures of Example 4, but employing the various optically active or racemic PGF$_{1\alpha}$ or 15β-PGF$_{1\alpha}$ type compounds, or their methyl esters, there are obtained the corresponding optically active or racemic 4,5-cis-didehydro-PGE$_1$ or 4,5-cis-didehydro-15β-PGE$_1$ type products within the scope of formulas VIII and XVI, for example:

4,5-cis-didehydro-19,20-dinor-PGE$_1$
dl-4,5-cis-didehydro-19,20-dinor-PGE$_1$
4,5-cis-didehydro-19,20-dinor-15β-PGE$_1$
dl-4,5-cis-didehydro-19,20-dinor-15β-PGE$_1$
4,5-cis-didehydro-16-ethyl-PGE$_1$
dl-4,5-cis-didehydro-16-ethyl-PGE$_1$
4,5-cis-didehydro-16-ethyl-15β-PGE$_1$
dl-4,5-cis-didehydro-16-ethyl-15β-PGE$_1$
4,5-cis-didehydro-16-fluoro-20-butyl-PGE$_1$
dl-4,5-cis-didehydro-16-fluoro-20-butyl-PGE$_1$
4,5-cis-didehydro-16-fluoro-20-butyl-15β-PGE$_1$
dl-4,5-cis-didehydro-16-fluoro-20-butyl-15β-PGE$_1$

EXAMPLE 5

4,5-cis-Didehydro-15-methyl-16-methyl-PGF$_{1\alpha}$, Methyl Ester (Formula IX: R$_1$ and R$_5$ are methyl, R$_x$ is 1-methylpentyl, and ~ is alpha).

1. Refer to Chart E. A solution of 4,5-cis-didehydro-16-methyl-PGF$_{1\alpha}$ methyl ester (Example 3, about 0.5 g.) in 24 ml. of dioxane is stirred at 50° C. under nitrogen and 2,3-dichloro-5,6-dicyano-1,4-benzoquinone (0.37 g.) is added. The mixture is stirred at 50° C. for 24 hrs., cooled to room temperature, and filtered. The filter cake is washed with tetrahydrofuran, and the filtrate and wash are combined and concentrated under reduced pressure. The residue is taken up in dichloromethane and washed with brine, then dried over sodium sulfate and concentrated under reduced pressure. The residue is chromatographed on silica gel, eluting with 2–10% ethanol in dichloromethane. Fractions shown by TLC to contain the desired product are combined and concentrated to give the formula-XLIX 15-oxo intermediate.

2. A solution of about 0.4 g. of the above 15-oxo compound, hexamethyldisilazane (3 ml.) and trimethylchlorosilane (0.5 ml.) in 20 ml. of tetrahydrofuran is allowed to stand at about 25° C. for 20 hrs. The mixture is filtered and the filtrate is concentrated by evaporation under reduced pressure. Xylene (10 ml.) is added to the residue and removed by evaporation under reduced pressure.

3. The residue of step 2 is dissolved in anhydrous ether and 110% of the theoretical amount of 3 M methyl magnesium bromide in ether is added. The mixture is allowed to stand 20 min. at about 25° C. and poured into 100 ml. of saturated aqueous ammonium chloride. The ether layer is separated, the aqueous layer is extracted with ether, and the ether extracts are combined and washed with brine, dried over sodium sulfate, and evaporated under reduced pressure. The residue is dissolved in 300 ml. of ethanol and 30 ml. of water containing 3 drops of glacial acetic acid, and the mixture is stirred for 2 hrs. at about 25° C. The mixture is concentrated under reduced pressure to an aqueous residue and the residue is extracted with dichloromethane. The dichloromethane extract is evaporated under reduced pressure to give a residue which is chromatographed over silica gel, eluting with 5%–10% ethanol in dichloromethane. Fractions shown by TLC to contain the desired product are combined and concentrated to yield the desired formula-IX title compound. Other fractions yield the 15-epimer corresponding to formula XVII.

EXAMPLE 6

4,5-cis-Didehydro-16-methyl-PGF$_{1β}$, Methyl Ester (Formula IX: R$_1$ is methyl, R$_5$ is hydrogen, R$_x$ is 1-methylpentyl, and ~ is beta).

Refer to Chart F. A solution of sodium borohydride (300 mg.) in 6 ml. of ice-cold methanol is added to a solution of 4,5-cis-didehydro-16-methyl-PGE$_1$, methyl ester (Example 4, 650 mg.) in 30 ml. of methanol at −5° C. The mixture is stirred for 0.5 hrs. at 0° C. and 5 ml. of acetone is added, after which the mixture is stirred for 5 min. and made slightly acid with acetic acid. The mixture is concentrated under reduced pressure until most of the methanol and acetone are removed, then the residue is extracted with dichloromethane. The extract is washed with water, dilute aqueous sodium bicarbonate, and brine, then dried over sodium sulfate and evaporated under reduced pressure to give a residue. This residue is chromatographed over silica gel, eluting with 2–10% ethanol in ethyl acetate. Those fractions containing the title compound free of starting material and impurities, as shown by TLC, are combined and concentrated to yield the formula-IX product.

EXAMPLE 7

4,5-cis-Didehydro-PGA$_1$ (Formula X: R$_1$ and R$_5$ are hydrogen, and R$_x$ is 1-methylpentyl).

Refer to Chart F. A solution of 4,5-cis-didehydro-16-methyl-PGE$_1$ methyl ester (Example 4, 300 mg.), 4 ml. of tetrahydrofuran and 4 ml. of 0.5 N hydrochloric acid is left standing at 25° C. for five days. Brine and dichloromethane-ether (1:3) are added and the mixture is stirred. The organic layer is separated, dried and concentrated. The residue is dissolved in ether which is washed with saturated aqueous sodium bicarbonate, dried and concentrated. The aqueous phase is quickly acidified with hydrochloric acid and extracted with dichloromethane which in turn is dried and concentrated. The residue is again dissolved in ether, extracted with aqueous sodium bicarbonate, and the aqueous phase is acidified with hydrochloric acid and extracted with dichloromethane. Finally, the organic phase is concentrated to yield the formula-X title compound.

EXAMPLE 8

4,5-cis-Didehydro-16-methyl-PGB$_1$ (Formula XI: R$_1$ and R$_5$ are hydrogen, and R$_x$ is 1-methylpentyl).

Refer to Chart F. A solution of 4,5-cis-didehydro-16-methyl-PGE$_1$ methyl ester (Example 4, 200 mg.) in 100 ml. of 50% aqueous ethanol containing about one gram of potassium hydroxide is kept at 25° C. for 10 hrs. under nitrogen. Then, the solution is cooled to 10° C. and neutralized by addition of 3 N. hydrochloric acid at 10° C. The resulting solution is extracted repeatedly with ethyl acetate, and the combined ethyl acetate extracts are washed with water and then with brine, dried, and concentrated to give the desired formula-XI title compound.

EXAMPLE 9

4,5-cis-Didehydro-13,14-dihydro-16-methyl-PGF$_{1\alpha}$
(Formula XIII: R$_1$ and R$_5$ are hydrogen, R$_x$ is
1-methylpentyl, and ~ is alpha).

1. Refer to Chart G. A solution of formula-LVII 3α,-5α-dihydroxy-2β-(3α-hydroxy-4-methyl-trans-1-octenyl)-1α-cyclopentanepropionaldehyde δ-lactol (Example 1, 100 mg.) in 10 ml. of ethyl acetate is shaken with hydrogen at about one atmosphere pressure at 25° C. in the presence of 5% rhodium on charcoal (15 mg.). After approximately one equivalent of hydrogen is absorbed, the hydrogenation is stopped, and the catalyst is removed by filtration. The filtrate is evaporated, and the residue is chromatographed on silica gel, eluting with 50–100% ethyl acetate gradient in Skellysolve B. Those fractions shown by TLC to contain the desired formula-LVIII product free of the starting product and hydrogenolysis products are combined and evaporated to give 3α,5α-dihydroxy-2β-(3α-hydroxy-4-methyloctyl)-1α-cyclopentanepropionaldehyde δ-lactol.

2. Following the procedures of Example 2 but replacing the formula-XXXVIII lactol of that example with the lactol of step 1 above, there is obtained the title compound.

Following the procedures of Example 9, but replacing the formula-LVII lactol with the corresponding formula-LVII 3β-hydroxy compound obtained following Example 1, there is obtained the corresponding formula-XXI 4,5-cis-didehydro-13,14-dihydro-16-methyl-PGF$_{1\alpha}$ product.

Likewise following the procedures of Example 9, but employing the various optically active or racemic 3α- or 3β-hydroxy lactols obtained following Example 1, for example wherein R$_x$ is propyl, 1-ethylpentyl, or 1-fluorononyl, there is obtained the corresponding optically active or racemic 4,5-cis-didehydro-13,14-dihydro-PGF$_{1\alpha}$ or 4,5-cis-didehydro-13,14-dihydro-15β-PGF$_{1\alpha}$ type product, within the scope of formulas XIII and XXI, for example:

4,5-cis-didehydro-13,14-dihydro-19,20-dinor-PGF$_{1\alpha}$
dl-4,5-cis-didehydro-13,14-dihydro-19,20-dinor-PGF$_{1\alpha}$
4,5-cis-didehydro-13,14-dihydro-19,20-dinor-15β-PGF$_{1\alpha}$
dl-4,5-cis-didehydro-13,14-dihydro-19,20-dinor-15β-PGF$_{1\alpha}$
4,5-cis-didehydro-13,14-dihydro-16-ethyl-PGF$_{1\alpha}$
dl-4,5-cis-didehydro-13,14-dihydro-16-ethyl-PGF$_{1\alpha}$
4,5-cis-didehydro-13,14-dihydro-16-ethyl-15β-PGF$_{1\alpha}$
dl-4,5-cis-didehydro-13,14-dihydro-16-ethyl-15β-PGF$_{1\alpha}$
4,5-cis-didehydro-13,14-dihydro-16-fluoro-20-butyl-PGF$_{1\alpha}$
dl-4,5-cis-didehydro-13,14-dihydro-16-fluoro-20-butyl-PGF$_{1\alpha}$
4,5-cis-didehydro-13,14-dihydro-16-fluoro-20-butyl-15β-PGF$_{1\alpha}$
dl-4,5-cis-didehydro-13,14-dihydro-16-fluoro-20-butyl-15β-PGF$_{1\alpha}$

EXAMPLE 10

4,5-cis-Didehydro-2a-homo-PGF$_{1\alpha}$ (Formula XXV: R$_1$ is hydrogen and ~ is alpha).

Refer to Chart H. A Wittig reagent prepared from (4-carboxybutyl)triphenylphosphonium bromide (1.77 g.) and sodio methylsulfinylcarbamide (from sodium hydride, 0.37 g. of 54%, in 6 ml. of dimethylsulfoxide) is combined with the formula-LXII lactol (Preparation 11, 0.32 g.) in 4 ml. of dimethylsulfoxide. The mixture is stirred about 17 hrs. at ambient temperature, diluted with about 50 ml. of benzene, and washed with potassium hydrogen sulfate solution. The benzene layer is washed with brine, dried, and evaporated. The residue is chromatographed over acid-washed silica gel. The column is eluted first with ethyl acetate and then ethyl acetate-5% methanol. Those fractions shown by TLC to contain the desired compound free of starting materials and impurities are combined and concentrated to yield the title compound, 0.035 g., mass spectral peaks (trimethylsilyl derivative) at 656, 641, 595, 566, 495, and 476.

Following the procedure of Example 10, but replacing the formula-LXII lactol with either the corresponding racemic lactol, the corresponding 3β-hydroxy lactol, or the corresponding racemic 3β-hydroxy lactol obtained following Preparation 11, there is obtained the corresponding product in each instance, namely dl-4,5-cis-didehydro-2a-homo-PGF$_{1\alpha}$, 4,5-cis-didehydro-2a-homo-15β-PGF$_{1\alpha}$, or dl-4,5-cis-didehydro-2a-homo-15β-PGF$_{1\alpha}$.

EXAMPLE 11

3α,5α-Dihydroxy-2β-(3α-hydroxy-4,4-dimethyl-trans-1-octenyl)-1α-cyclopentanepropionaldehyde
δ-Lactol (Formula XXXVIII: R$_x$ is 1,1-dimethylpentyl and ~ OH is alpha).

I. Refer to Chart B. The starting material of Formula XXXVI wherein R$_x$ is 1,1-dimethylpentyl is obtained by the procedure of Preparations 1–10 starting with the optically active formula-XXVII iodolactone of Preparation 1, but in Preparation 5 replacing racemic ethyl 2-methylhexanoate with ethyl 2,2-dimethylhexanoate. The dimethyl 2-oxo-3,3-dimethylheptylphosphonate thus obtained is used in Preparation 6 to yield the corresponding formula-XXXII product. Thereafter, by the procedures of Preparations 7-10, there is obtained the formula-XXXVI 3α,5α-dihydroxy-2β-(3α-hydroxy-4,4-dimethyl-trans-1-octenyl)-1α-cyclopentaneacetaldehyde γ-lactol, 3,3'-bis(tetrahydropyranyl)ether wherein R$_x$ is 1,1-dimethylpentyl.

A mixture of sodium hydride (2.77 g. of 59%) and 40 ml. dimethyl sulfoxide is heated at 65°–70° C. for about 2 hr., then cooled to about 15° C. To the clear solution of sodio methylsulfinylcarbanide thus obtained is added methoxymethyltriphenylphosphonium chloride (23.8 g.) with vigorous stirring. After about 10 min., with cooling, there is added the lactol XXXVI above (15 g.) in 30 ml. of dimethyl sulfoxide, dropwise and the mixture allowed to warm to about 25° C. while stirring for about 16 hr. Upon chilling, the mixture yields about 10 g. of byproducts which are rinsed with diethyl ether and filtered off. The filtrate is concentrated under reduced pressure, to an oil. The oil is subjected to silica gel chromatography, eluting with acetone-Skellysolve B (15-85). Those fractions shown by thin-layer chromatography (TLC) to contain the formula-XXXVII intermediate are combined and concentrated to yield that enol-ether.

II. The formula-XXXVII intermediate is transformed stepwise to the formula-XXXVIII title compound as follows. The enol-ether (9.91 g.) is treated in 500 ml. of methanol with 200 ml. of a pH 2 buffer solution, thereafter isolating the methyl ether of the formula-XXXVIII lactol. For this purpose, the methanol is partially removed, brine is added, and the mixture extracted with chloroform. The chloroform extracts are washed, dried, and concentrated to an oil (6.72 g.).

The title compound is obtained by treating the above methyl ether in 250 ml. of tetrahydrofuran with 125 ml. of a pH 1.0 buffer solution at about 25° C. When the reaction is complete as shown by TLC, in approximately 27 hr., brine is added plus solid sodium chloride. The organic layer is washed, dried, and concentrated to the formula-XXXVIII lactol (6.0 g.) having NMR peaks at 5.55 and 0.89 δ, and infrared absorption at 3380, 1665, and 975 cm$^{-1}$.

EXAMPLE 12

$3\alpha,5\alpha$-Dihydroxy-$2\alpha$-(3-hydroxy-4,4-dimethyl-trans-1-octenyl)-1$\alpha$-cyclopentanepropionaldehyde δ-Lactol, 4,3'-bis(tetrahydropyranyl)ether.

The 4,3'-bis(tetrapyranyl)ether of the formula-XXXVIII product of Example 11 is prepared in several steps as follows.

I. To a suspension of silver oxide (prepared from 1.14 g. of silver nitrate and 6.8 ml. of 2N. sodium hydroxide solution in water) is added the formula-XXXVIII lactol (1.0 g.) in 4 ml. of tetrahydrofuran while cooling in an ice bath and stirring for 1.75 hr. After filtering off the solids, the combined washings and filtrate are washed with diethyl ether. The aqueous layer is chilled, acidified with 10% potassium hydrogen sulfate solution to a pH less than 2, treated with brine, and extracted with dichloromethane and again with diethyl ether. The extracts are dried, and concentrated to an oil (0.746 g.) comprising the substituted propionic acid.

II. A portion of the above oil (0.565 g.) is treated in dichloromethane solution with pyridine hydrochloride until lactone formation is complete, in about 4 hr.

III. The lactone above, in dichloromethane, is next treated with dihydropyran (1.25 ml.) at about 25° C. for 16 hr. until both hydroxyl groups are transformed to tetrahydropyranyloxy groups. The mixture is washed with 10% sodium bicarbonate solution, and then with brine. The dichloromethane layer is dried over magnesium sulfate and concentrated under reduced pressure to an oil, 1.069 g.

IV. The product of step III above is finally reduced to the title δ-lactol as follows. The lactone bis(tetrahydropyranyl)ether above (1.069 g.) in 125 ml. of toluene is treated at about −50° C. with diisobutylaluminum hydride (10% in toluene, 8 ml.) added dropwise with stirring. After a total of 20 min., the mixture is treated with tetrahydrofuran-water (2:1) and stirred at about 25° C. for 1 hr. The mixture is filtered, washed with brine, dried over magnesium sulfate, and concentrated to an oil, 1.13 g. The oil is subjected to silica gel chromatography, eluting with 10% acetone in dichloromethane, to yield the title compound, 0.627 g.

EXAMPLE 13

4,5-cis-Didehydro-16,16-dimethyl-PGF$_{1\alpha}$, 11,15-bis(tetrahydropyranyl)ether, Methyl Ester.

I. Following the procedure of Example 2, but replacing the formula-XXXVIII lactol of that example with the product of Example 12, and subjecting the product to silica gel chromatography there is obtained 4,5-cis-didehydro-16,16-dimethyl-PGF$_{1\alpha}$, 11,15-bis(tetrahydropyranyl)-ether, 0.794 g.

II. The above free acid product is converted to the title compound by reaction with diazomethane in dichloromethane, thereafter recovering the title compound, an oil, 0.373 g.

EXAMPLE 14

4,5-cis-Didehydro-16,16-dimethyl-PGE$_1$, Methyl Ester (Formula VIII: R$_1$ is methyl, R$_5$ is hydrogen, and R$_x$ is 1,1-dimethylpentyl).

A solution of the product of Example 13 (0.271 g.) in 10 ml. of acetone is treated at about −18° C. with Jones reagent (0.2 ml.) (see J. Chem. Soc. 39 (1946)) and the mixture stirred for 10 min. Thereafter, 0.25 ml. of isopropyl alcohol is added, and the reaction mixture is diluted with brine and extracted with ethyl acetate. The extract is washed with ice-cold dilute sodium bicarbonate solution, then brine, and dried over magnesium sulfate. After concentration under reduced pressure, there is left an oil (0.250 g.). The oil is treated with 5 ml. of a mixture of acetic acid-water-tetrahydrofuran (30:15:4), heated at 45° C. for 4.5 hrs. The mixture is cooled, diluted with brine, and extracted with ethyl acetate. The extract is washed with cold dilute sodium bicarbonate and water, dried, and concentrated to an oil. The oil (0.181 g.) is combined with 0.055 g. from a similar preparation and subjected to silica gel chromatography, eluting with ethyl acetate-Skellysolve B (1:1). There is obtained the title compound, an oil, 0.152 g., having infrared, absorption at 3420, 1740, and 975 cm$^{-1}$; mass spectral peaks (for TMS desivative) at 523, 507, 448, 439, 433, and 417; and NMR peaks at 5.69, 5.35, 3.69, 2.35, and 0.88 δ.

EXAMPLE 15

4,5-cis-Didehydro-16,16-dimethyl-PGF$_{1\alpha}$ (Formula IX: R$_1$ and R$_5$ are hydrogen, R$_x$ is 1,1-dimethylpentyl, and ~ is alpha) and Methyl Ester (Formula IX: R$_1$ is methyl, R$_5$ is hydrogen, R$_x$ is 1,1-dimethylpentyl, and ~ is alpha).

I. Refer to Chart B. Following the procedure of Example 2, but replacing the formula-XXXVIII lactol of that example with the product of Example 11 (0.502 g.), there is obtained an oil. This oil is subjected to silica gel chromatography, eluting with ethyl acetate-benzene (3:2), to yield the formula-IX acid title compound, an oil, 0.856 g.

II. The acid product above (0.717 g.), is treated in dichloromethane-ethyl ether with diazomethane. The reaction mixture is concentrated and the residue is subjected to silica gel chromatography, eluting with acetone-dichloromethane (1:1). There is obtained the methyl ester title compound, 0.721 g., having mass spectral peaks (for the trimethylsilyl derivative) at 581, 522, 513, 423, and 217; infrared absorption at 3380, 1740, and 970 cm$^{-1}$; and NMR peaks at 5.43, 4.39-3.60, 3.67, 2.34, and 0.88 δ.

I claim:
1. An optically active compound of the formula

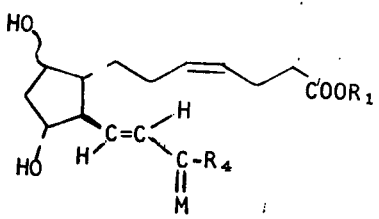

or a racemic compound of that formula and the mirror image thereof, wherein M is

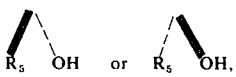

wherein $R_5$ is hydrogen, methyl, or ethyl; wherein $R_1$ is hydrogen or alkyl or one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein $R_4$ is alkyl of 6 to 10 carbon atoms, inclusive, substituted with zero to 2 fluoro, inclusive; including the lower alkanoates thereof, and the pharmacologically acceptable salts thereof when $R_1$ is hydrogen.

2. 4,5-cis-Didehydro-16,16-dimethyl-$PGF_{1\alpha}$, a compound according to claim 1.

3. 4,5-cis-Didehydro-16,16-dimethyl-$PGF_{1\alpha}$, methyl ester, a compound according to claim 1.

4. A compound according to claim 1 wherein $R_4$ has a chain length of 6 carbon atoms.

5. 4,5-cis-Didehydro-20-methyl-$PGF_{1\alpha}$, a compound according to claim 4.

6. 4,5-cis-Didehydro-20-methyl-$PGF_{1\alpha}$, methyl ester, a compound according to claim 4.

7. 4,5-cis-Didehydro-16-fluoro-20-methyl-$PGF_{1\alpha}$, a compound according to claim 4.

8. 4,5-cis-Didehydro-16-fluoro-20-methyl-$PGF_{1\alpha}$, methyl ester, a compound according to claim 4.

9. 4,5-cis-Didehydro-16,16-difluoro-20-methyl-$PGF_{1\alpha}$, a compound according to claim 4.

10. 4,5-cis-Didehydro-16,16-difluoro-20-methyl-$PGF_{1\alpha}$, methyl ester, a compound according to claim 4.

* * * * *

UNITED STATES PATENT OFFICE
CERTIFICATE OF CORRECTION

Patent No. 3,933,889            Dated 20 January 1976

Inventor(s) Barney J. Magerlein

It is certified that error appears in the above-identified patent and that said Letters Patent are hereby corrected as shown below:

Column 3, line 6, "$PGF_2\beta$" should read -- $PGF_2\alpha$ --.
Column 9, line 59, "$PGF_1$" should read -- $PGF_1\alpha$ --.
Column 14, lines 23-24, "$-CH(CH_3)-(CH_2-CH_3,$" should read -- $-CH(CH_3)-(CH_2)_2-CH_3$, --.
Column 14, line 51, "dihyro" should read -- dihydro --.
Column 15, line 29, "-propanol, 1-propanol," should read -- -1-propanol, --.
Column 24, line 39, "=50°" should read -- -50° --.
Column 25, line 21, "=10°" should read -- -10° --.
Column 25, line 51, "PkGF-type" should read -- PGF-type --.
Column 28, line 65, "PGF - type" should read -- $PGF\beta$-type --.
Column 31, line 26, "XVII" should read -- XVIII --.
Column 32, line 57, "$PGF_1$" should read -- $PGF_1\alpha$ --.
Column 43, line 52, "$-PGF_1$" should read -- $PGF_1\alpha$ --.
Column 49, line 24, "$-2\alpha-(3-hydroxy-$" should read -- $-2\beta-(3\alpha-hydroxy-$ --.

Signed and Sealed this

Twenty-first Day of July 1981

[SEAL]

Attest:

Attesting Officer

GERALD J. MOSSINGHOFF

Commissioner of Patents and Trademarks